(12) United States Patent
Ohno et al.

(10) Patent No.: US 7,193,030 B2
(45) Date of Patent: Mar. 20, 2007

(54) ACID ANHYDRIDE AND POLYIMIDE USING THE SAME

(75) Inventors: Daisuke Ohno, Tokyo (JP); Kenji Ishii, Tokyo (JP); Yasumasa Norisue, Tokyo (JP); Masamitchi Mizukami, Tokyo (JP); Atsushi Hirashima, Tokyo (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 314 days.

(21) Appl. No.: 10/868,799

(22) Filed: Jun. 17, 2004

(65) Prior Publication Data

US 2004/0258852 A1    Dec. 23, 2004

(30) Foreign Application Priority Data

Jun. 18, 2003 (JP) ............................ 2003-173507
Jul. 28, 2003 (JP) ............................ 2003-281121
Apr. 5, 2004 (JP) ............................ 2004-110926

(51) Int. Cl.
*C08G 73/10* (2006.01)
*C08G 65/331* (2006.01)
*C08G 65/332* (2006.01)

(52) U.S. Cl. ............... 528/335; 528/44; 528/84; 528/176; 528/191; 528/219; 528/347; 525/397; 525/420

(58) Field of Classification Search ............... 528/170, 528/353, 172–173, 219, 191, 335, 347, 44, 528/84, 176; 549/241; 525/397, 420
See application file for complete search history.

(56) References Cited

U.S. PATENT DOCUMENTS 3,981,847 A    9/1976 Meyer et al.

| 5,140,077 | A |   *   | 8/1992  | Sivavec et al. ............. 525/397 |
| 5,189,115 | A |       | 2/1993  | Melquist ..................... 525/420 |
| 6,962,744 | B2 |  *   | 11/2005 | Amagai et al. ........... 428/297.4 |
| 6,995,195 | B2 |  *   | 2/2006  | Ishii et al. .................. 522/181 |
| 2004/0258852 | A1 | * | 12/2004 | Ohno et al. ................ 428/1.26 |

FOREIGN PATENT DOCUMENTS

| DE | 23 57 297 | | 5/1975 |
| EP | 1 384 733 | | 1/2004 |
| JP | 11-116675 | * | 4/1999 |
| WO | WO 02/102756 | | 12/2002 |

* cited by examiner

*Primary Examiner*—Ana Woodward
(74) *Attorney, Agent, or Firm*—Wenderoth, Lind & Ponack, L.L.P.

(57) ABSTRACT

An acid anhydride of the formula (4), and a polyimide using the acid anhydride,

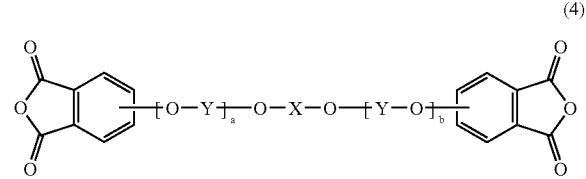

(4)

wherein anhydrides are substituted at sites 3 or sites 4, which acid anhydride is obtained from, as a raw material, a bifunctional phenylene ether oligomer having a number average molecular weight of 500 to 3,000, represented by the formula (1).

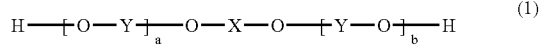

(1)

13 Claims, 10 Drawing Sheets

IR spectrum of Resin B in Example 1

IR spectrum of Resin C in Example 1

IR spectrum of Acid anhydride D in Example 1

¹H-NMR spectrum of Resin B in Example 1

¹H-NMR spectrum of Resin C in Example 1

$^1$H-NMR spectrum of Acid anhydride D in Example 1

IR spectrum of Acid anhydride H in Example 2

IR spectrum of Acid anhydride I in Example 3

IR spectrum of Acid anhydride J in Example 4

IR spectrum of Acid anhydride K in Example 5

¹H-NMR spectrum of Acid anhydride H in Example 2

¹H-NMR spectrum of Acid anhydride I in Example 3

¹H-NMR spectrum of Acid anhydride J in Example 4

¹H-NMR spectrum of Acid anhydride K in Example 5

IR spectrum of Acid anhydride L in Example 6

$^1$H-NMR spectrum of Acid anhydride L in Example 6

IR spectrum of Polyimide O in Example 9

IR spectrum of Polyimide P in Example 10

ACID ANHYDRIDE AND POLYIMIDE USING THE SAME

FIELD OF THE INVENTION

The present invention relates to a novel acid anhydride obtained from a bifunctional phenylene ether oligomer having a specific structure as a raw material, and a polyimide using the above acid anhydride. The acid anhydride of the present invention can be used as a raw material for polyamic acid, a raw material for polyimide, an epoxy resin curing agent, etc., and is useful as a polymer material excellent in heat resistance, low dielectric characteristics and low moisture absorptivity. Polymer materials obtained from the acid anhydride of the present invention as a raw material are useful for wide applications such as an electrical insulating material, a molding material, a resin for a copper-clad laminate, a resin for a resist, a sealing resin for electronic parts, a resin for a color filter of liquid crystal, a coating composition, various coating agents, an adhesive, a buildup laminate material, a resin for a flexible substrate and a functional film.

PRIOR ARTS OF THE INVENTION

Conventionally, acid anhydrides are widely used as a raw material for functional polymer materials such as a polyamic acid, polyimide and a thermosetting epoxy resin. With a recent increase in required performance in these application fields, physical properties required as a functional polymer material become severer increasingly. As such physical properties, for example, there are required heat resistance, weather resistance, chemical resistance, low moisture absorptivity, high fracture toughness, low dielectric constant, low dielectric loss tangent, moldability, transparency and flexibility. In a printed circuit board material field, for example, a substrate material having low dielectric characteristics is desired from a signal fade problem attendant upon high-frequency of a signal. In a flexible substrate field, a material having lower dielectric characteristics than those of a conventional polyimide and a material excellent in processability are required. A novel acid anhydride and a polyimide obtained from the above acid anhydride have been developed (for example, JP-A-11-116675).

On the other hand, similar anhydrides have been also studied for the purpose of improving the processability of polyether imide (JP-B-4-69651). Anhydrides using a polyphenylene ether oligomer are used in these prior technical documents, while these documents do not disclose the compound of the present invention.

SUMMARY OF THE INVENTION

It is an object of the present invention to provide a novel acid anhydride which is used as a raw material for obtaining a polymer material having high heat resistance, low dielectric constant, low dielectric loss tangent and low moisture absorptivity, and a polyimide using the above acid anhydride.

The present invention 1 provides an acid anhydride of the formula (4), and a polyimide from it,

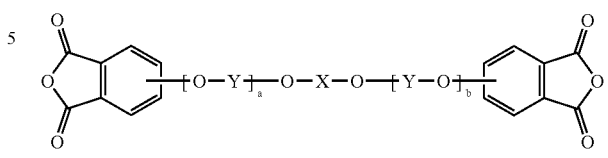

wherein anhydrides are substituted at sites 3 or sites 4,
—O—X—O— is formed of a structure defined by the formula (2),

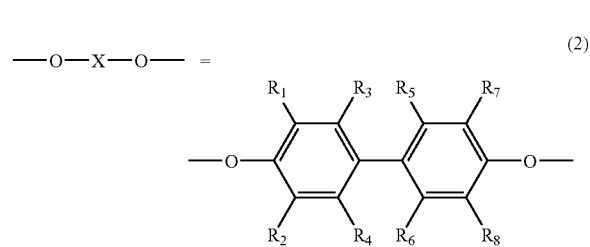

in which $R_1$, $R_2$, $R_3$, $R_7$ and $R_8$ may be the same or different and represent a halogen atom, an alkyl group having 6 or less carbon atoms or a phenyl group and $R_4$, $R_5$ and $R_6$ may be the same or different and represent a hydrogen atom, a halogen atom, an alkyl group having 6 or less carbon atoms or a phenyl group, —[Y—O]— is an arrangement of one kind of structure defined by the formula (3) or a random arrangement of at least two kinds of structures defined by the formula (3),

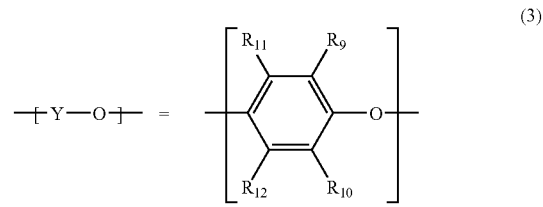

in which $R_9$ and $R_{10}$ may be the same or different and represent a halogen atom, an alkyl group having 6 or less carbon atoms or a phenyl group and $R_{11}$ and $R_{12}$ may be the same or different and represent a hydrogen atom, a halogen atom, an alkyl group having 6 or less carbon atoms or a phenyl group, and each of a and b is an integer of 0 to 30, provided that at least one of a and b is not 0, which acid anhydride is obtained from, as a raw material, a bifunctional phenylene ether oligomer having a specific structure represented by the formula (1),

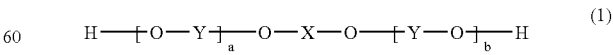

wherein —O—X—O—, —[Y—O]—, a and b are as defined in the formula [4].

The present invention 2 provides an acid anhydride of the formula (11), and a polyimide using the above acid anhydride, (11)

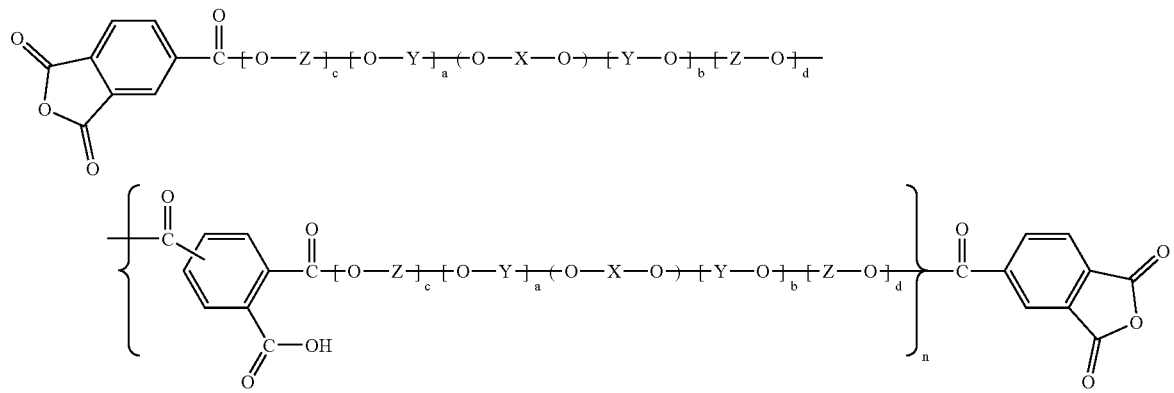

wherein —(O—X—O)— is formed of a structure defined by the formula (2) or the formula (10), (2)

—(O—X—O)— =

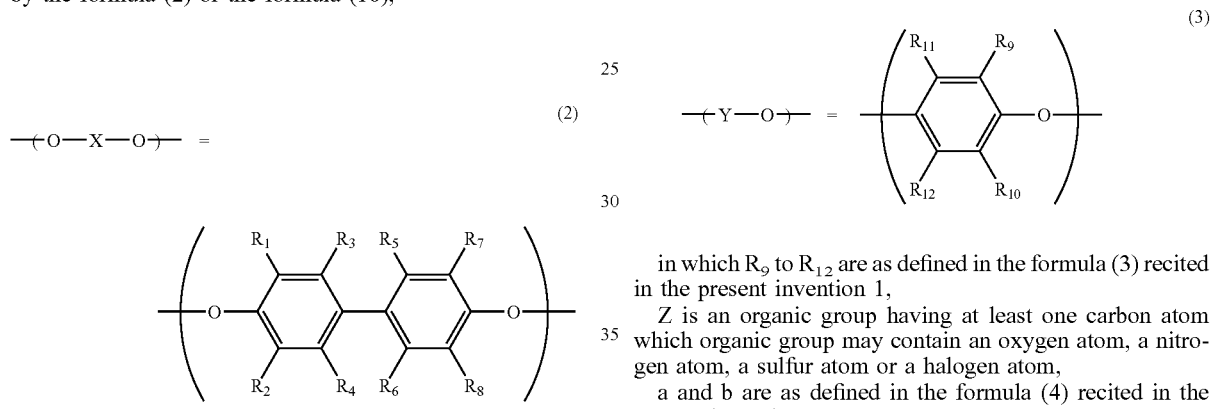

in which $R_1$ to $R_8$ are as defined in the formula (2) recited in the present invention 1, (10)

—(O—X—O)— = in which $R_{13}$, $R_{14}$, $R_{19}$ and $R_{20}$ may be the same or different and represent a halogen atom, an alkyl group having 6 or less carbon atoms or a phenyl group, $R_{15}$, $R_{16}$, $R_{17}$ and $R_{18}$ may be the same or different and represent a hydrogen atom, a halogen atom, an alkyl group having 6 or less carbon atoms or a phenyl group and A is a linear, branched or cyclic hydrocarbon having 20 or less carbon atoms, —(Y—O)— is an arrangement of one kind of structure defined by the formula (3) or a random arrangement of at least two kinds of structures defined by the formula (3), (3)

in which $R_9$ to $R_{12}$ are as defined in the formula (3) recited in the present invention 1, Z is an organic group having at least one carbon atom which organic group may contain an oxygen atom, a nitrogen atom, a sulfur atom or a halogen atom, a and b are as defined in the formula (4) recited in the present invention 1, each of c and d is 0 or 1, and n is an integer of 0 to 10, which acid anhydride is obtained from, as a raw material, a bifunctional phenylene ether oligomer having a number average molecular weight of 500 to 3,000, represented by the formula (9), (9)

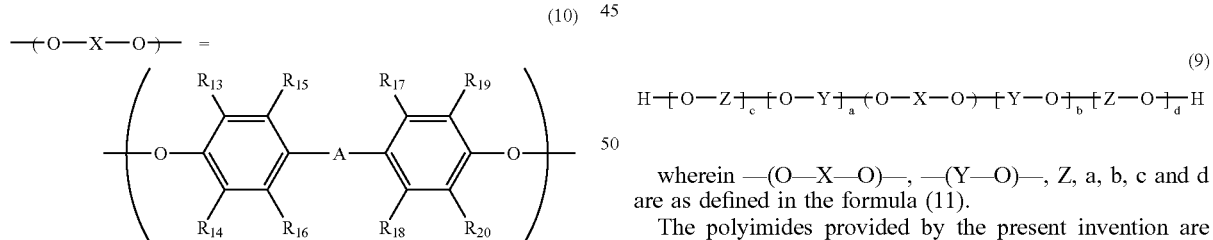

wherein —(O—X—O)—, —(Y—O)—, Z, a, b, c and d are as defined in the formula (11).

The polyimides provided by the present invention are obtained by reacting the acid anhydride of the present invention 1 or the present invention 2 with a diamine or a diisocyanate.

DETAILED DESCRIPTION OF THE INVENTION

Figure 1:
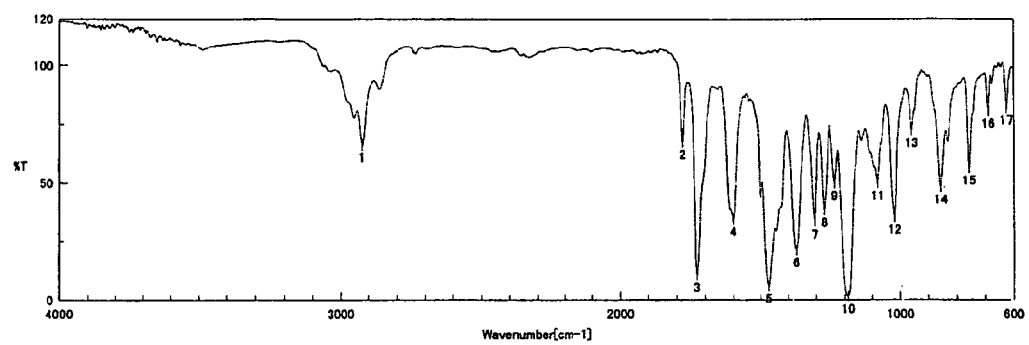
FIG. 1 shows the IR spectrum of a resin B in Example 1.

The present inventors have developed a bifunctional phenylene ether oligomer having the excellent dielectric characteristics and heat resistance of a polyphenylene ether structure and having a specific structure and various derivatives using the above oligomer. As a result of further diligent studies, the present inventors have found that a terminal acid anhydride can be derived from the bifunctional phenylene ether oligomer. On the basis of the above finding, the present inventors have completed the present invention.

The present invention will be explained in detail hereinafter. First, in the compound of the formula (1) of the present invention 1, —O—X—O— is represented by the formula (2), in which $R_1$, $R_2$, $R_3$, $R_7$ and $R_8$ may be the same or different and represent a halogen atom, an alkyl group having 6 or less carbon atoms or a phenyl group and $R_4$, $R_5$ and $R_6$ may be the same or different and represent a hydrogen atom, a halogen atom, an alkyl group having 6 or less carbon atoms or a phenyl group. —[Y—O]— is an arrangement of one kind of structure defined by the formula (3) or a random arrangement of at least two kinds of structures defined by the formula (3), in which $R_9$ and $R_{10}$ may be the same or different and represent a halogen atom, an alkyl group having 6 or less carbon atoms or a phenyl group and $R_{11}$ and $R_{12}$ may be the same or different and represent a hydrogen atom, a halogen atom, an alkyl group having 6 or less carbon atoms or a phenyl group. Each of a and b is an integer of 0 to 30, provided that at least one of a and b is not 0. In the above formulae, preferably, $R_1$, $R_2$, $R_3$, $R_7$, $R_8$, $R_9$ and $R_{10}$ represent an alkyl group having 3 or less carbon atoms and $R_4$, $R_5$, $R_6$, $R_{11}$ and $R_{12}$ represent a hydrogen atom or an alkyl group having 3 or less carbon atoms. When the molecular weight is too small, electric characteristics, which the phenylene ether structure has, cannot be obtained. When the molecular weight is too large, the reactivity of a terminal functional group decreases. For these reasons, the compound of the formula (1) preferably has a number average molecular weight of 500 to 3,000.

The process for the production of the bifunctional phenylene ether oligomer of the formula (1) is not specially limited and it can be produced by any process. For example, the bifunctional phenylene ether oligomer of the formula (1) can be produced by oxidative coupling of a bifunctional phenol compound and a monofunctional phenol compound in the presence of copper and an amine according to a method disclosed by JP-A-2003-12796, JP-A-2003-212990, Japanese patent application No. 2002-279389 or Japanese patent application No. 2002-018508.

Then, the acid anhydride of the present invention will be explained. The process for producing the acid anhydride represented by the above formula (4) is not specially limited and it may be produced by any process. For example, it can be produced by reacting the compound represented by the formula (1) and 4-nitrophthalimide represented by the formula (13) and then carrying out the steps of hydrolysis and dehydration. When a phthalimide nitrated at site 3 is used as a raw material, it can be substituted at site 3. These processes can utilize a conventional process and, for example, processes disclosed in JP-A-50-24242, J.Polym.Sci.Polym. Chem.Ed.23, 1759–1769(1985), etc., can be used.

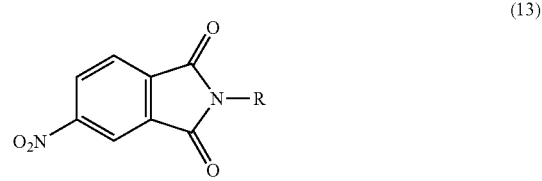

(13)

The acid anhydride of the present invention 1, obtained as described above, can be suitably used as a raw material for polyamic acid or polyimide (polyether imide) or as a curing agent for an epoxy resin.

Then, the present invention 2 will be explained in detail. First, in the compound represented by the formula (9), —(O—X—O)— is represented by the formula (2) in which $R_1$ to $R_8$ are as defined in the formula (2) recited in the present invention 1, or the formula (10) in which $R_{13}$, $R_{14}$, $R_{19}$ and $R_{20}$ may be the same or different and represent a halogen atom, an alkyl group having 6 or less carbon atoms or a phenyl group and $R_{15}$, $R_{16}$, $R_{17}$ and $R_{18}$ may be the same or different and represent a hydrogen atom, a halogen atom, an alkyl group having 6 or less carbon atoms or a phenyl group.

A is a linear, branched or cyclic hydrocarbon having 20 or less carbon atoms. —(Y—O)— is an arrangement of one kind of structure defined by the formula (3) or a random arrangement of at least two kinds of structures defined by the formula (3), in which $R_9$ and $R_{10}$ may be the same or different and represent a halogen atom, an alkyl group having 6 or less carbon atoms or a phenyl group and $R_{11}$ and $R_{12}$ may be the same or different and represent a hydrogen atom, a halogen atom, an alkyl group having 6 or less carbon atoms or a phenyl group. Z is an organic group which has at least one carbon atom and may contain an oxygen atom, a nitrogen atom, a sulfur atom or a halogen atom. Each of a and b is an integer of 0 to 30, provided that at least one of a and b is not 0. Each of c and d is 0 or 1. In the above formulae, $R_1$, $R_2$, $R_3$, $R_7$, $R_8$, $R_{13}$, $R_{14}$, $R_{19}$ and $R_{20}$ preferably represent an alkyl group having 3 or less carbon atoms, $R_4$, $R_5$, $R_6$, $R_{15}$, $R_{16}$, $R_{17}$ and $R_{18}$ preferably represent a hydrogen atom or an alkyl group having 3 or less carbon atoms, $R_9$ and $R_{10}$ preferably represent an alkyl group having 3 or less carbon atoms, and $R_{11}$ and $R_{12}$ preferably represent a hydrogen atom or an alkyl group having 3 or less carbon atoms. When the molecular weight is too small, electric characteristics which the phenylene ether structure has can not be obtained. When it is too large, the reactivity of a terminal functional group decreases. For these reasons, the compound of the formula (9) preferably has a number average molecular weight of 500 to 3,000.

The process for producing the bifunctional phenylene ether oligomer represented by the formula (9) is not specially limited and it can be produced by any process. For example, it can be produced by oxidatively coupling a bifunctional phenol compound and a monofunctional phenol compound in the presence of copper and an amine according to a method disclosed in JP-A-2003-12796, Japanese patent application No. 2002-279389 or Japanese patent application No. 2002-018508, to produce a compound of the formula (1), and optionally introducing —(Z—O)— as required.

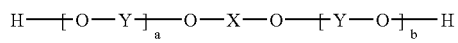
(1)

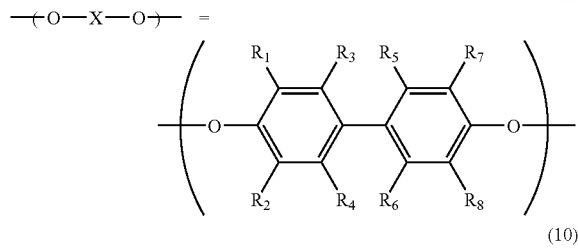
(2)

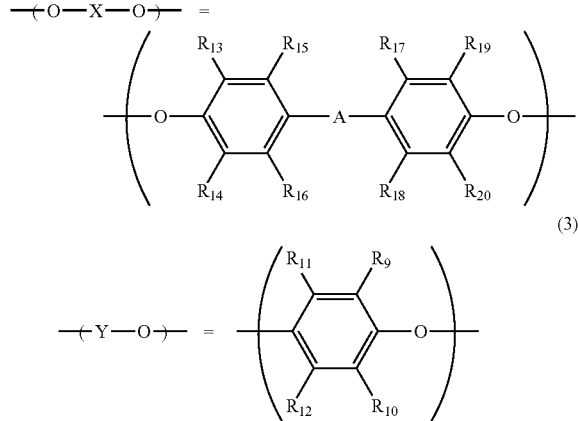
(3)

(wherein —(O—X—O)— is represented by the formula (2) in which $R_1$, $R_2$, $R_3$, $R_7$ and $R_8$ may be the same or different and represent a halogen atom, an alkyl group having 6 or less carbon atoms or a phenyl group and $R_4$, $R_5$ and $R_6$ may be the same or different and represent a hydrogen atom, a halogen atom, an alkyl group having 6 or less carbon atoms or a phenyl group, or the formula (10) in which $R_{13}$, $R_{14}$, $R_{19}$ and $R_{20}$ may be the same or different and represent a halogen atom, an alkyl group having 6 or less carbon atoms or a phenyl group, $R_{15}$, $R_{16}$, $R_{17}$ and $R_{18}$ may be the same or different and represent a hydrogen atom, a halogen atom, an alkyl group having 6 or less carbon atoms or a phenyl group and A is a linear, branched or cyclic hydrocarbon having 20 or less carbon atoms, —(Y—O)— is an arrangement of one kind of structure defined by the formula (3) or a random arrangement of at least two kinds of structures defined by the formula (3), in which $R_9$ and $R_{10}$ may be the same or different and represent a halogen atom, an alkyl group having 6 or less carbon atoms or a phenyl group and $R_{11}$ and $R_{12}$ may be the same or different and represent a hydrogen atom, a halogen atom, an alkyl group having 6 or less carbon atoms or a phenyl group, and each of a and b is an integer of 0 to 30, provided that at least one of a and b is not 0.)

At Z, an organic group having at least one carbon atom (which may contain an oxygen atom, a nitrogen atom, a sulfur atom or a halogen atom) may be placed. Examples of -(Z—O—)— include —((CH$_2$)$_i$—O)—, —(CH$_2$CHRO)$_j$—, —(CH$_2$—Ar—O)—, etc., while it is not limited these examples. A method of addition is typically a method in which -(Z—O—)— is directly added to an intermediate represented by the formula (1) or a method in which a halide is used, while it is not specially limited to these methods.

A case of introducing, for example, —(CH$_2$)$_i$O— or —(CH$_2$CHR$_{21}$O)$_j$— as -(Z—O—)— will be explained. —(CH$_2$)$_i$O— is introduced by reacting the compound of the formula (1) with a halogenated alcohol of the formula (14) in a proper solvent such as alcohol, ether or ketone in the presence of an alkali catalyst such as KOH, K$_2$CO$_3$ or NaOEt. —(CH$_2$CHR$_{21}$O)$_j$— is introduced by reacting the compound of the formula (1) with an alkylene oxide of the formula (15) in a benzene type solvent such as benzene, toluene or xylene in the presence of an alkali catalyst such as KOH, NaOEt or triethylamine according to, for example, a method disclosed in JP-B-52-4547.

(14)

wherein E represents Cl or Br, and i is an integer of 2 or more.

(15)

wherein $R_{21}$ represents a hydrogen atom, a methyl group or an ethyl group.

Then, the acid anhydride of the present invention will be explained. The process for producing the acid anhydride represented by the formula (11) is not specially limited and it can be produced by any process. For example, it can be obtained by reacting the compound of the formula (9) and trimellitic anhydride chloride in the presence of a base such as pyridine or triethylamine. As a solvent, there may be used a solvent unreactive with acid anhydride or acid chloride, such as toluene, xylene, dichloromethane or chloroform. The reaction is preferably carried out under an atmosphere of an inert gas such as nitrogen or argon for preventing any deactivation of acid anhydride or acid chloride.

Further, the acid anhydride of the present invention can be obtained by reacting the compound of the formula (9) with trimellitic anhydride in the presence of a condensing agent. The condensing agent includes known esterification agents such as sulfuric acid. As a solvent, there may be used a solvent unreactive with acid anhydride, such as toluene or xylene. The reaction is preferably carried out under an atmosphere of an inert gas such as nitrogen or argon for preventing any deactivation of acid anhydride.

The acid anhydride of the present invention 2, obtained as above, can be suitably used as a raw material for polyamic acid or polyimide or as a curing agent for an epoxy resin.

Then, the polyimide of the present invention will be explained based on the present invention 2. The polyimide of the present invention can be produced through a polyamic acid by reacting the acid anhydride of the formula (11) with a diamine. Further, the polyimide of the present invention can be directly produced by reacting the acid anhydride of the formula (11) with a diisocyanate. These production processes are generally known and disclosed in "Jikken Kagaku Koza (Courses in Experimental Chemistry), 4th Ed., Vol.28, Koubunshi Gosei (Polymer Synthesis)", edited by The Chemical Society of Japan and published by Maruzen, pp312–313 and pp319–320, etc.

For producing the polyimide of the present invention, the acid anhydride represented by the formula (11) is used alone or a mixture of at least two acid anhydrides represented by the formula (11) is used. Further, it is preferable to use a different bifunctional acid anhydride other than the acid anhydride of the formula (11) in combination with the acid anhydride of the formula (11). Particularly, when the acid anhydride of the formula (11) is used in combination with a bifunctional acid anhydride represented by the formula (16) or the formula (17), an improvement in heat resistance is found. For this reason, when the polyimide of the present invention is used for an application in which heat resistance is required, it is more preferable to use these bifunctional acid anhydrides in combination with the acid anhydride of the formula (11). Further, it is possible to add a small amount of a trifunctional acid anhydride as a crosslinking agent.

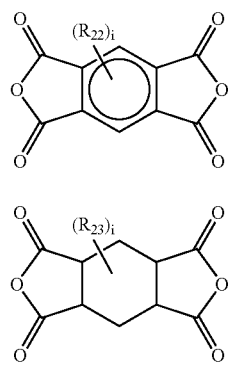

(in the formulae 16 and 17, $R_{22}$ and $R_{23}$ each represent hydrogen, an alkyl group having 1 to 6 carbon atoms, trifluoromethyl, a hydroxyl group or a halogen, and i is an integer of 1 to 4.)

The diamine to be reacted with the acid anhydride of the present invention is not specially limited so long as it is a divalent amine. The diamine is preferably diamines represented by the formula (18) to the formula (23). In the formulas (18) to (23), $R_{24}$ to $R_{37}$ each represent hydrogen, an alkyl group having 1 to 6 carbon atoms, trifluoromethyl, a hydroxyl group or a halogen, each of i, j, k and l is independently an integer of 1 to 3, and Q is methylene, ethylene, ethylidene, trimethylene, propylene, propylidene, butylidene, hexafluoroisopropylidene, oxygen, ketone, sulfur, sulfoxide or sulfone. The site of substitution of propylidene or butylidene may be arbitrary. Nuclear hydrogenated products of these may be suitably used. The diamine may be used alone or a mixture of at least two diamines may be used. Further, it is possible to add a small amount of a crosslinking agent such as a triamine, as required. Furthermore, there may be used a trimethylsilylated diamine, disclosed in "Jikken Kagaku Koza (Courses in Experimental Chemistry), 4th Ed., Vol.28, Koubunshi Gosei (Polymer Synthesis)", edited by The Chemical Society of Japan and published by Maruzen, p317, which is a variation of the present process.

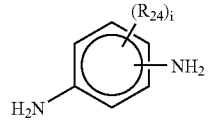
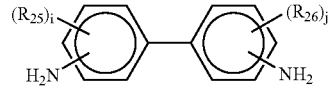
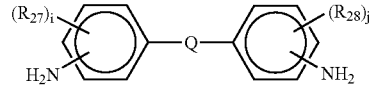
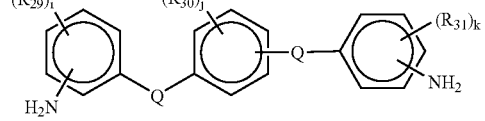
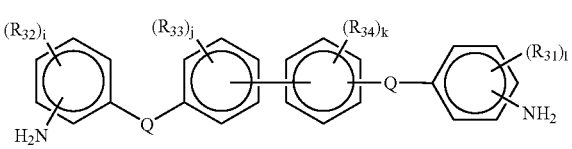

When the diamine is used, a polyamic acid as an intermediate is synthesized firstly. The polyamic acid is a polyamide having a carboxylic acid in a side chain, which is obtained by reacting a divalent acid anhydride and a divalent amine in a solvent. The synthesis of the polyamic acid in the present invention is carried out by dissolving a divalent amine in a solvent and then adding the acid anhydride of the formula (11) to the resultant solution, to react the divalent amine and the acid anhydride of the formula (11) while dissolving the acid anhydride of the formula (11). In the synthesis, the mixing order can be reversed. The solvent and reaction conditions for the synthesis of the polyamic acid are not specially limited. The solvent is preferably an amide solvent such as N,N-dimethylacetamide or N-methyl-2-pyrrolidinone or an ether solvent such as diethylene glycol dimethyl ether. The reaction temperature is preferably 10° C. to 100° C. When the temperature is low, the reaction does not proceed. When the temperature is too high, imidization which is the next stage partially proceeds, so that the uniformity of a resin is impaired. Generally, the thus-obtained polyamic acid solution is directly used in the next step, while purification or a concentration adjustment may be carried out before the next step.

The obtained polyamic acid solution is air-dried or dropwise added to a poor solvent to remove the solvent, whereby a solid polyamic acid can be obtained. The solid polyamic acid is heated or chemically treated, whereby the polyimide of the present invention can be obtained. For example, the polyamic acid solution is cast on a plain surface and dried to obtain a film, and then the film is heated under an inert gas atmosphere, whereby a film of the polyimide of the present invention can be obtained. When the polyimide is obtained by heating, the heating temperature is suitably 50 to 300° C. The polyimide can be obtained by chemical treatment in place of heating. For example, a polyamic acid film is immersed in a mixed solution of acetic anhydride and pyridine, whereby a film of the polyimide of the present invention can be obtained.

Then, a process using a diisocyanate will be explained. The diisocyanate usable in the present invention is not specially limited so long as it is a divalent isocyanate. Preferably, there may be used a diisocyanate obtained by replacing amino groups of anyone of the diamines of the formulae (18) to (23) with isocyanate groups. The diisocyanate may be used alone or a mixture of at least two diisocyanates may be used. Further, it is possible to add a small amount of a crosslinking agent such as a triisocyanate, as required.

When the diisocyanate is used, the reaction proceeds in one stage, so that the polyimide is directly generated without through an intermediate. The reaction conditions for producing the polyimide of the present invention are not specially limited. The reaction temperature is preferably 50 to 200° C. A solvent is not specially limited so long as it is inactive in the reaction. Examples thereof include an amide solvent such as N-methyl-2-pyrrolidinone, a nitrile solvent such as benzonitrile, a nitro solvent such as nitrobenzene and an ether solvent such as diethylene glycol dimethyl ether. Further, the reaction can be accelerated by adding a tertiary amine as a catalyst. As described above, the polyimide of the present invention is produced.

Effect of the Invention

The acid anhydride of the present invention is remarkably useful as a raw material for a highly-functional polymer material having a low dielectric constant, a low dielectric loss tangent and a low moisture absorptivity. The highly-functional polymer material obtained therefrom can be used, as a material excellent in electric characteristics and moldability, for wide applications such as an electrical insulating material, a molding material, a resin for a copper-clad laminate, a resin for a resist, a sealing resin for electronic parts, a resin for a color filter of liquid crystal, a coating composition, various coating agents, an adhesive, a buildup laminate material, a resin for a flexible substrate and a functional film.

EXAMPLES

The present invention will be explained more concretely with reference to Examples hereinafter, while the present invention shall not be specially limited to these Examples. Number average molecular weights and weight average molecular weights were measured according to the gel permeation chromatography (GPC) method (calculated as polystyrene). Tetrahydrofuran (THF) was used as a developing solvent for GPC.

Synthetic Example 1

Synthesis of Bifunctional Phenylene Ether Oligomer

A longitudinally long reactor having a volume of 100 liters and equipped with a stirrer, a thermometer, an air-introducing tube and baffleplates was charged with 4.61 g (20.8 mmol) of $CuBr_2$, 9 g (52 mmol) of N,N'-di-t-butyl-ethylenediamine, 333.8 g (3.3 mol) of n-butyldimethylamine and 26 kg of toluene. The components were stirred at a reaction temperature of 40° C. A mixed solution (molar ratio of a bivalent phenol of the formula (2): a monovalent phenol of the formula (3)=1:5) was obtained by dissolving 1.29 kg (4.8 mol) of 2,2',3,3',5,5'-hexamethyl- (1,1'-biphenyl)-4,4'-diol (to be referred to as "HMBP" hereinafter), 2.02 kg (24 mol) of 2,6-dimethylphenol, 6 g (35 mmol) of N,N'-di-t-butylethylenediamine and 129.8 g (1.28 mol) of n-butyldimethylamine in 23 kg of methanol, in advance. The mixed solution was dropwise added to the mixture in the reactor over 230 minutes while carrying out bubbling with 5.2 L/min of a mixed gas of nitrogen and air which gas had an oxygen concentration of 8%, and stirring was carried out. After the completion of the addition, 1.5 kg of water in which 236 g (623 mmol) of tetrasodium ethylenediamine tetraacetate was dissolved was added to the stirred mixture to terminate the reaction. An aqueous layer and an organic layer were separated. Then, the organic layer was washed with 1.0N hydrochloric acid aqueous solution and then washed with pure water. The thus-obtained solution was concentrated by an evaporator and then dried under a reduced pressure, to obtain 2.95 kg of a resin A represented by the formula (1). The resin A had a number average molecular weight of 1,068 and a weight average molecular weight of 1,736.

Example 1

Synthesis of Acid Anhydride

[Synthesis of Phthalimide]

A 500-ml reactor equipped with a stirrer, a thermometer, a Dean-Stark trap, a reflux tube and a nitrogen line was charged with 15.99 g of the resin A, and nitrogen replacements were carried out with three times. Then, 100 ml of dimethyl sulfoxide, 90 ml of toluene and 2.58 g (NaOH 0.032 mol) of 50% sodium hydroxide aqueous solution were added and the resultant mixture was refluxed under heat under nitrogen for 7 hours. During the refluxing, 7 ml of water was distilled off. Thereafter, 57 ml of toluene was distilled off over 40 minutes, and the heating was terminated at the time when the temperature of the reaction liquid came to 145° C. The reaction liquid was allowed to cool down to room temperature. 8.56 g (0.032 mol) of N-phenyl-4-nitro-phthalimide was added to the reaction liquid, and the mixture was stirred under heat at 60° C. for 3 hours. After the completion of the reaction, the reactor was allowed to cool, 3 ml of acetic acid was added, then, 200 ml of water was added, and the mixture was sufficiently stirred. A precipitated solid was filtered, washed with 30 ml of acetonitrile three times and air-dried, to obtain 19.66 g of a resin B having the following structure. The resin B had a number average molecular weight of 1,398 and a weight average molecular weight of 2,205. The structure was confirmed by a nuclear magnetic resonance spectrum and an infrared spectrum.

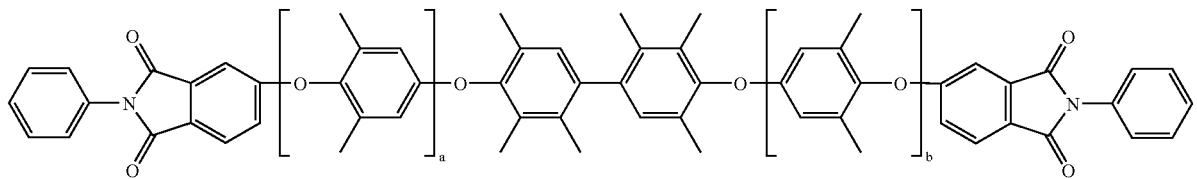

Synthesis of Amic Acid

A 300-ml reactor equipped with a stirrer and a thermometer was charged with 100 ml of tetrahydrofuran, 20 ml of water, 2.96 g (NaOH 0.037 mol) of 50% sodium hydroxide aqueous solution and 18.02 g of the resin B, and the mixture was stirred under heat at 40–44° C. 6 hours later, the heating was terminated, and the reactor was allowed to stand overnight. The reaction liquid was poured to dilute hydrochloric acid (35% hydrochloric acid:water=10:45, 165 ml), to precipitate a solid. The solid was filtered, washed with water and air-dried, and then, the solid was washed with 30 ml of acetonitrile and air-dried, to obtain 18.07 g of a resin C having the following structure. The structure was confirmed by a nuclear magnetic resonance spectrum and an infrared spectrum.

Figure 2:
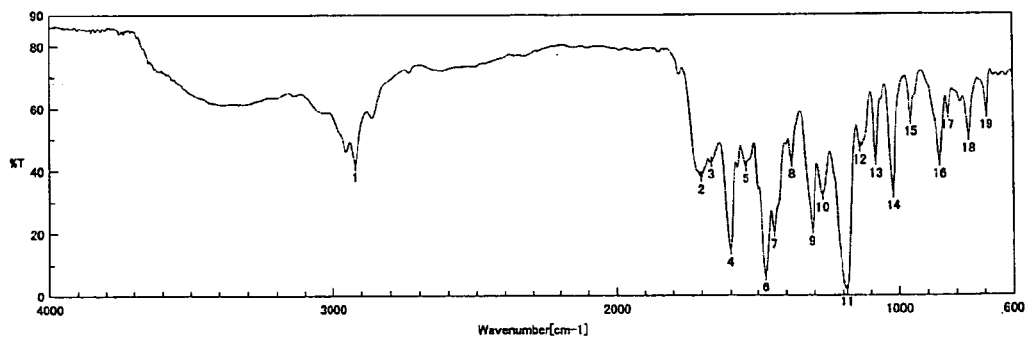
FIG. 2 shows the IR spectrum of a resin C in Example 1.
Figure 3:
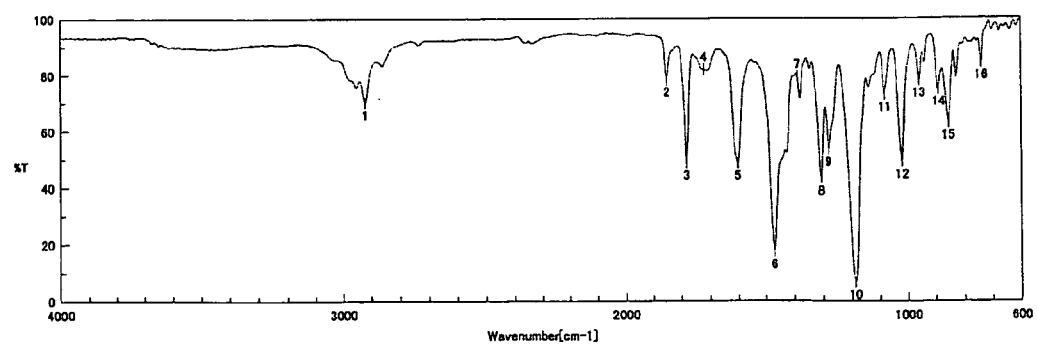
FIG. 3 shows the IR spectrum of an acid anhydride D in Example 1.

FIGS. 1 to 3 show the IR spectrums of the compounds obtained in Example 1.

Figure 4:
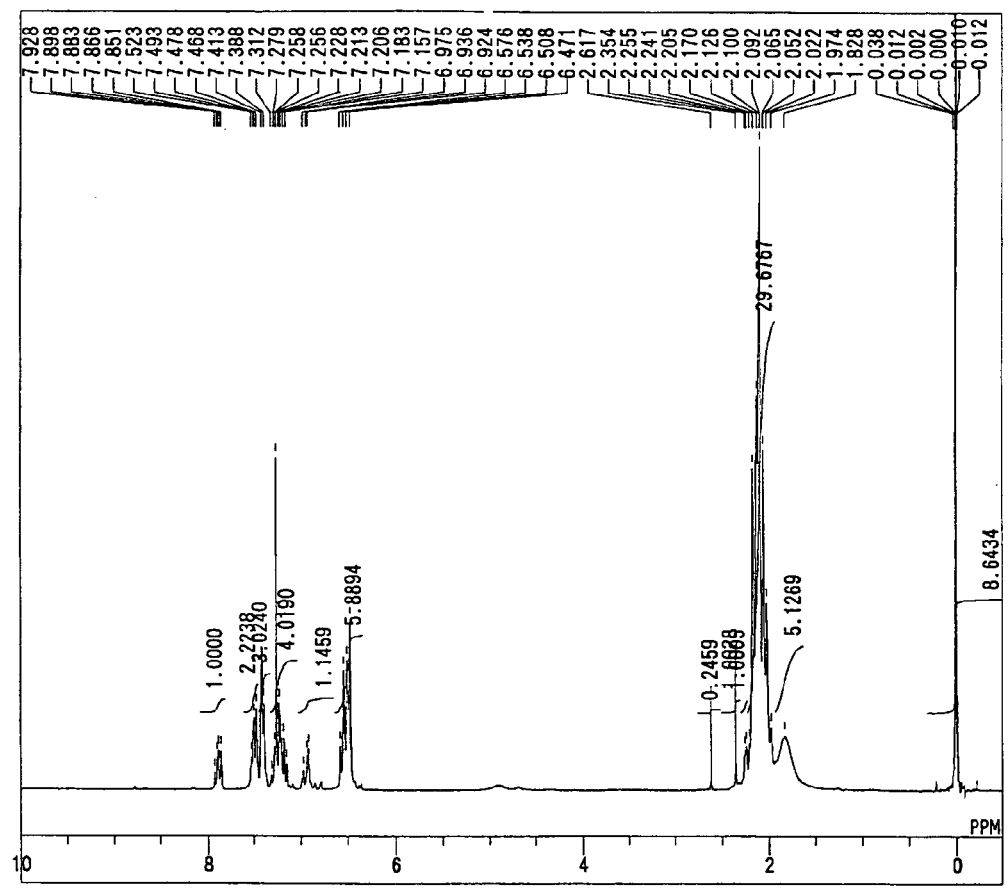
FIG. 4 shows the $^1$H-NMR spectrum of a resin B in Example
Figure 5:
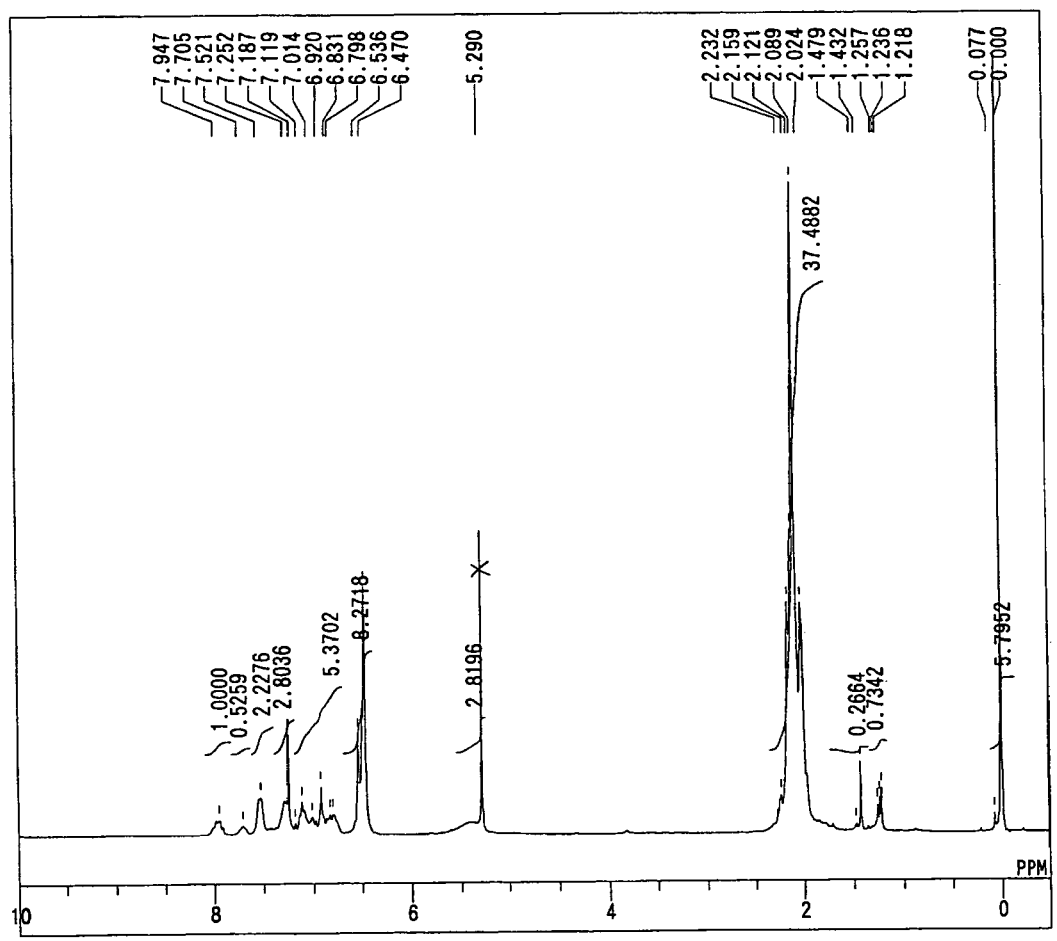
FIG. 5 shows the $^1$H-NMR spectrum of a resin C in Example 1.
Figure 6:
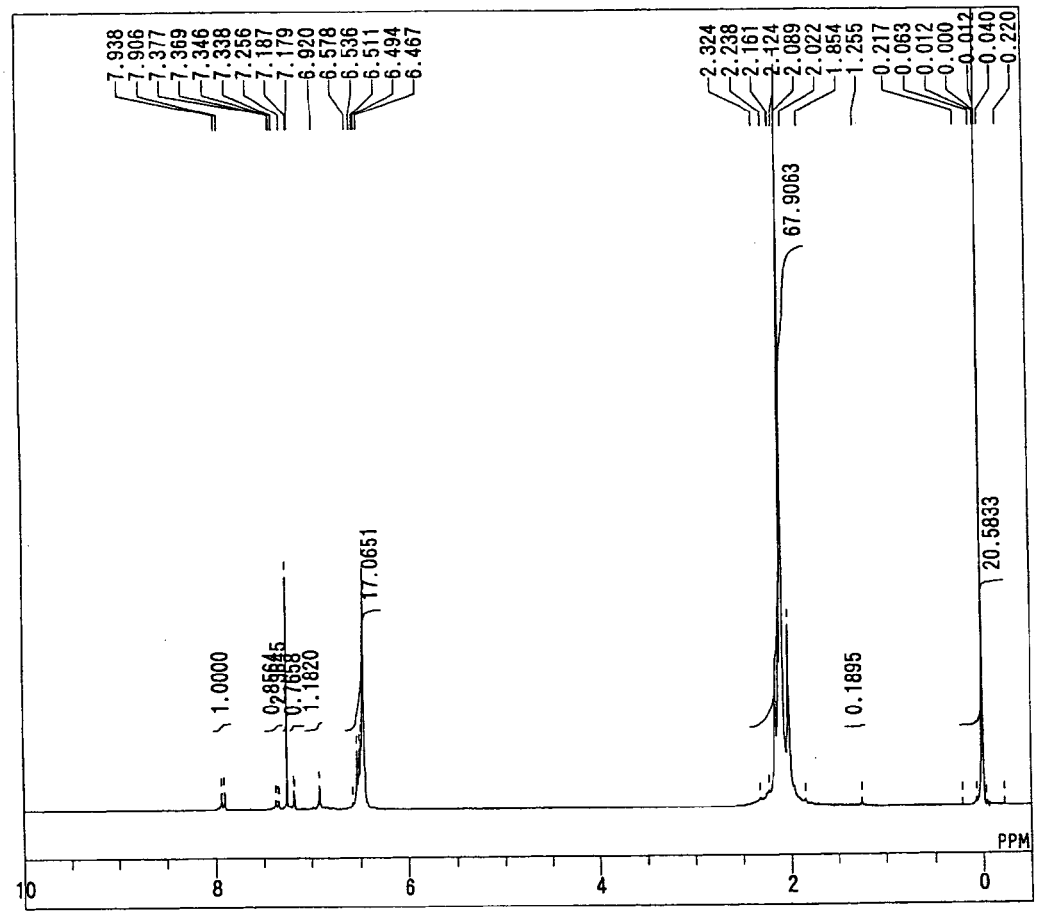
FIG. 6 shows the $^1$H-NMR spectrum of an acid anhydride D in Example 1.
Figure 7:
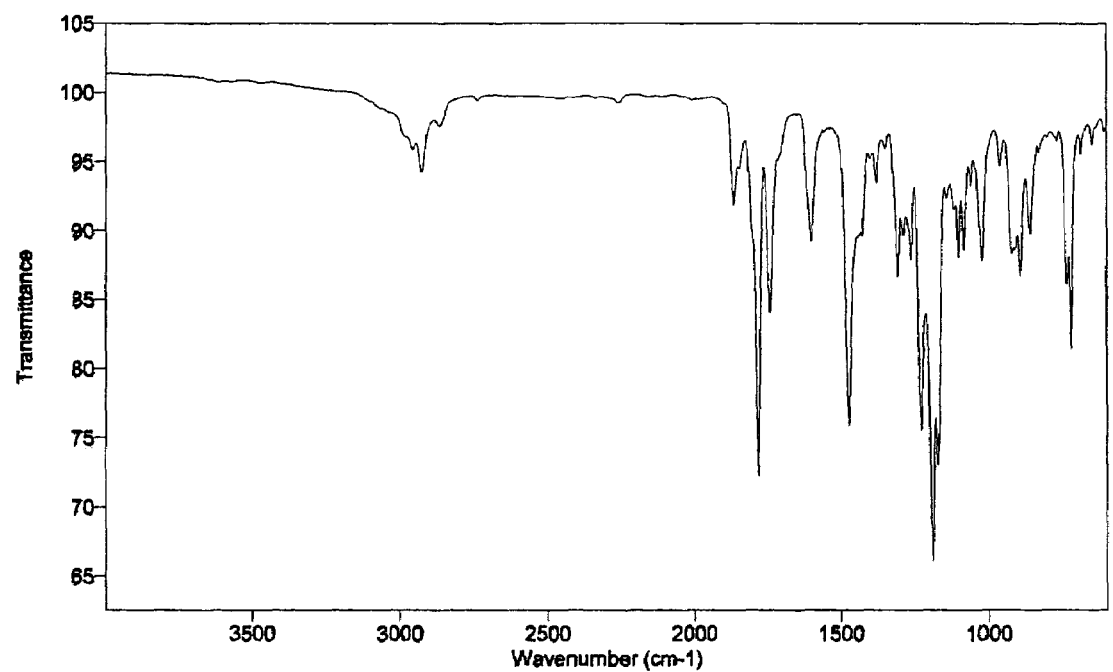
FIG. 7 shows the IR spectrum of an acid anhydride H in Example 2.
Figure 8:
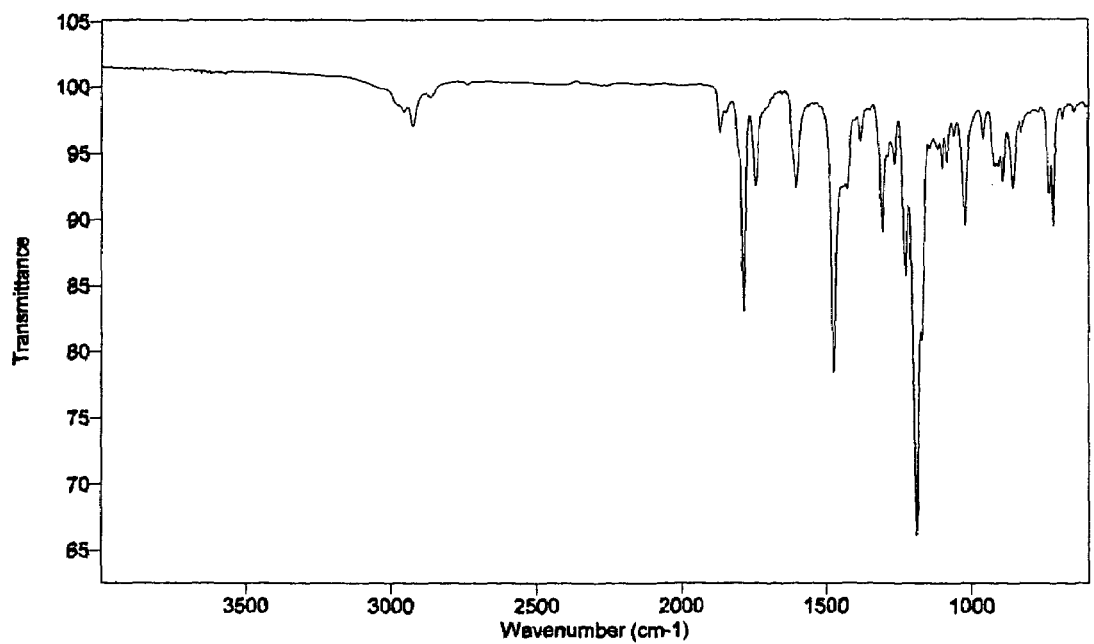
FIG. 8 shows the IR spectrum of an acid anhydride I in Example 3.
Figure 9:
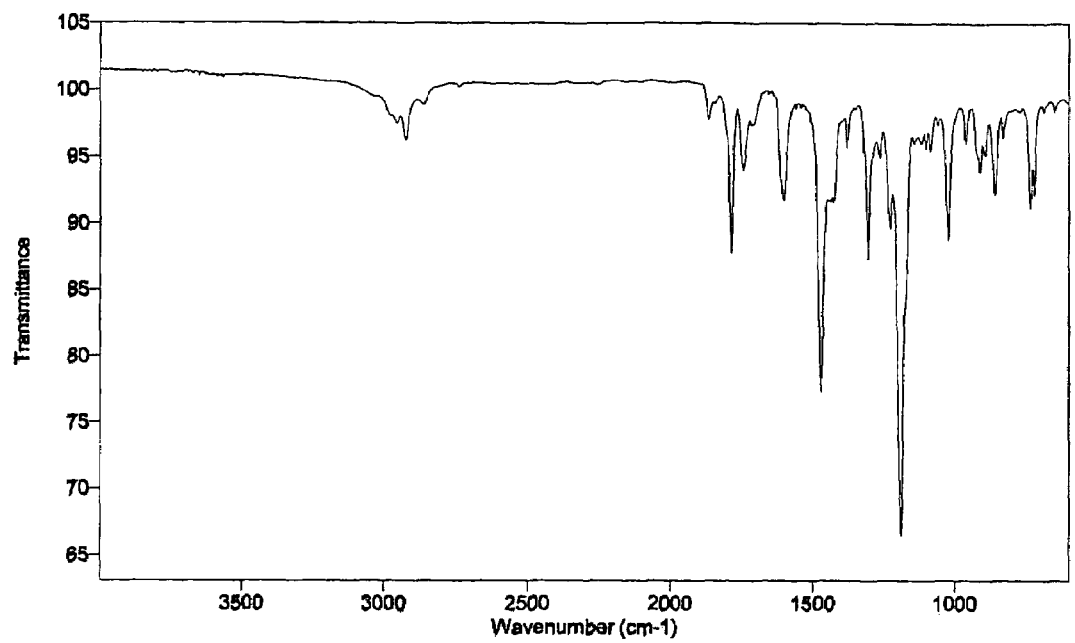
FIG. 9 shows the IR spectrum of an acid anhydride J in Example 4.
Figure 10:
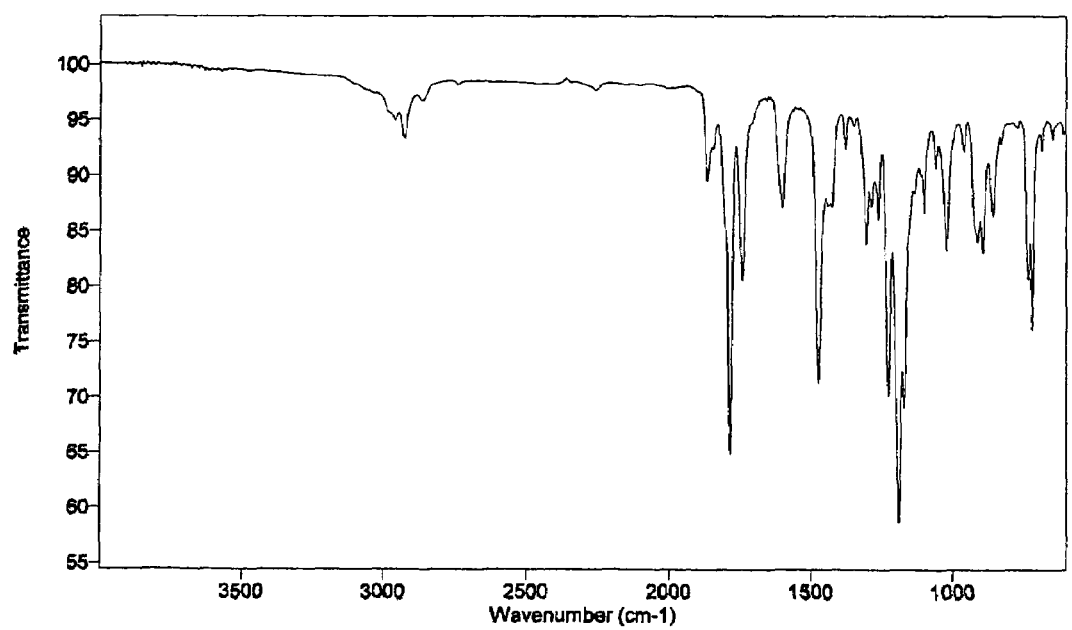
FIG. 10 shows the IR spectrum of an acid anhydride K in Example 5.
Figure 11:
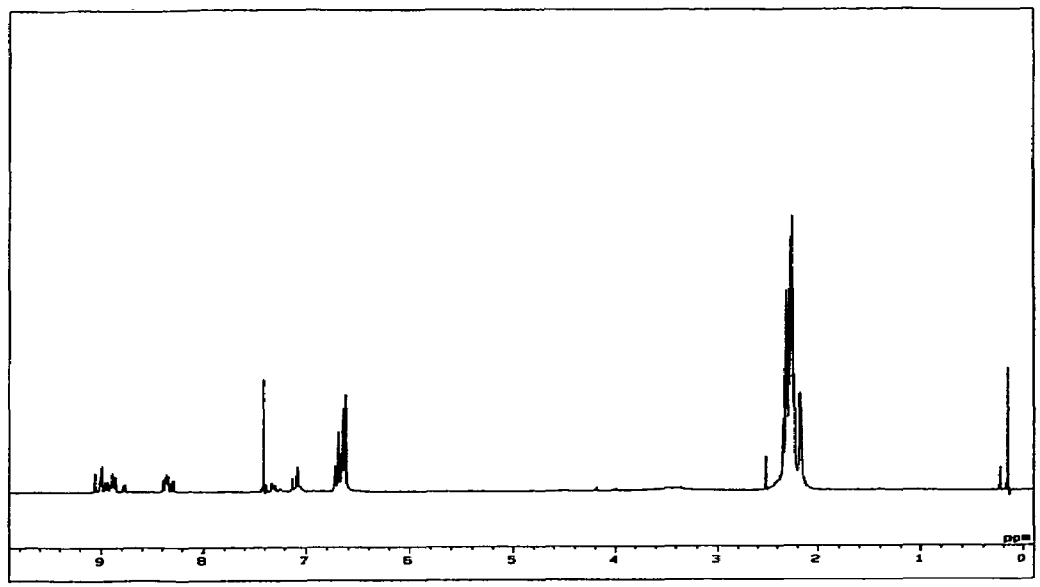
FIG. 11 shows the $^1$H-NMR spectrum of an acid anhydride H in Example 2.
Figure 12:
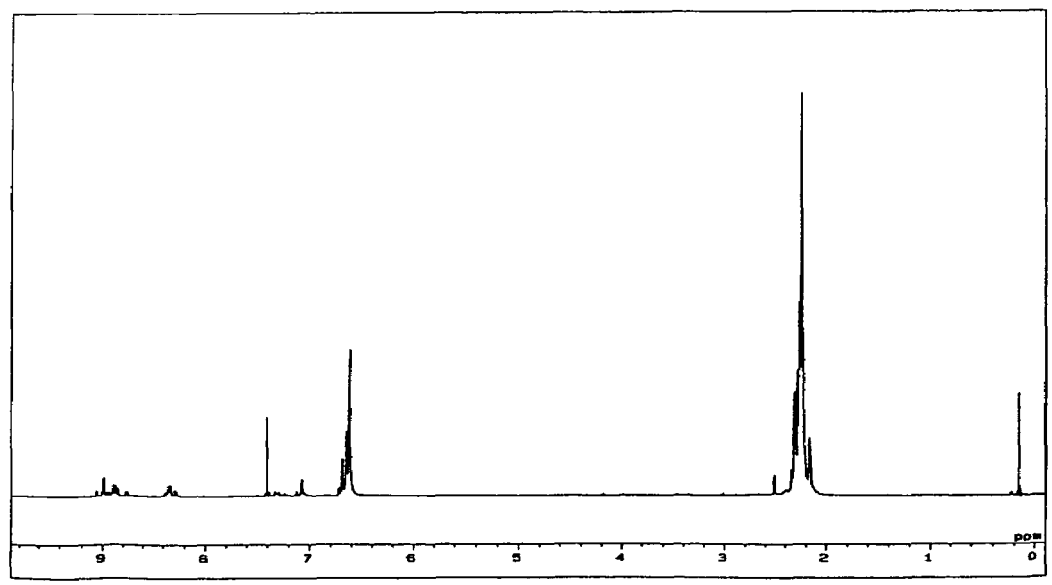
FIG. 12 shows the $^1$H-NMR spectrum of an acid anhydride I in Example 3.
Figure 13:
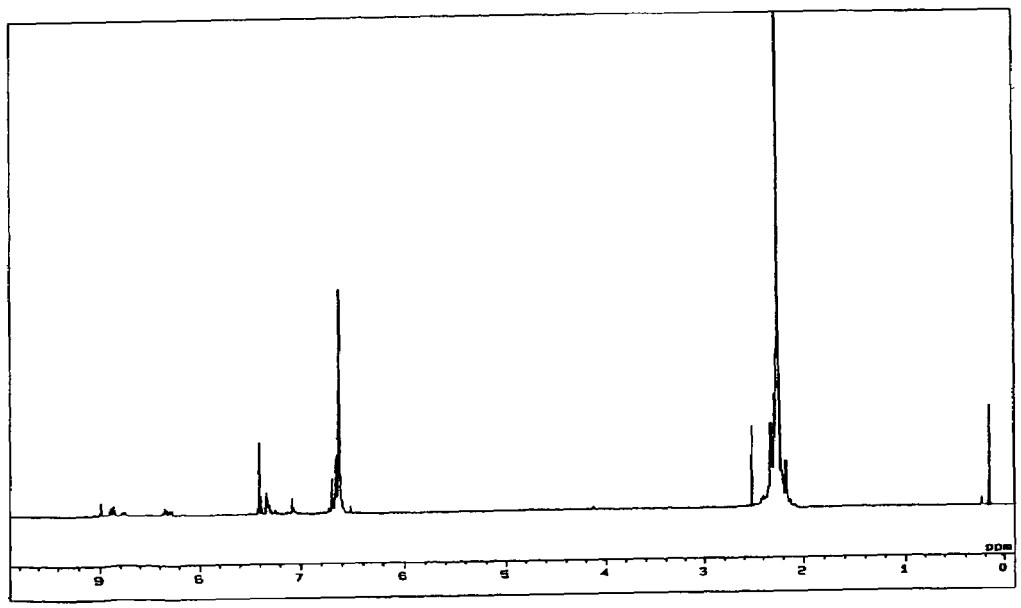
FIG. 13 shows the $^1$H-NMR spectrum of an acid anhydride J in Example 4.
Figure 14:
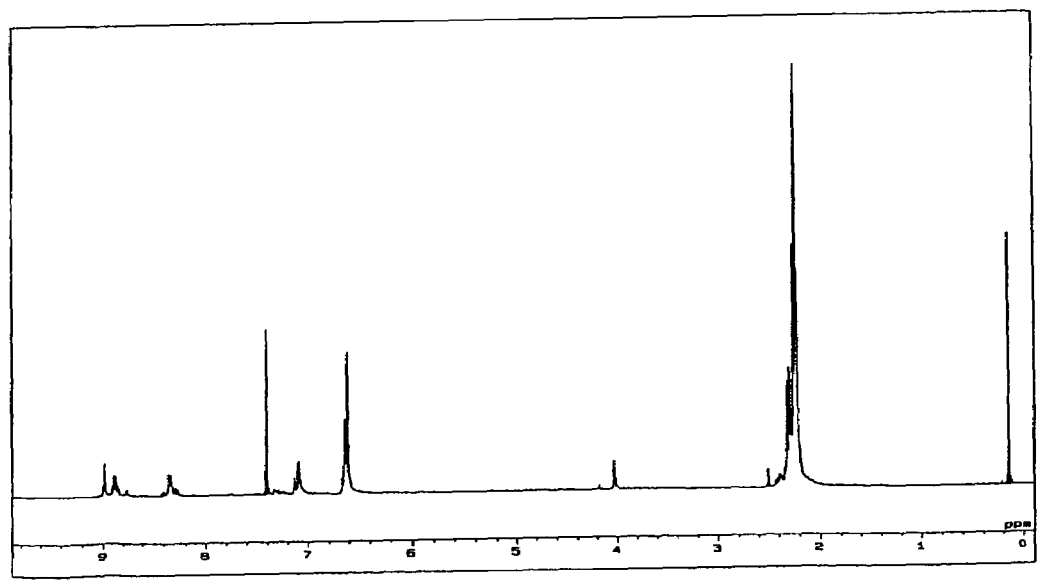
FIG. 14 shows the $^1$H-NMR spectrum of an acid anhydride K in Example 5.

FIGS. 4 to 6 show the NMR spectrums of the compounds obtained in Example 1.

The present invention 2 will be explained more concretely with reference to Examples hereinafter.

A number average molecular weight and a weight average molecular weight were measured according to the gel permeation chromatography (GPC) method (calculated as polystyrene). Tetrahydrofuran (THF) was used as a developing solvent for GPC. A hydroxyl group equivalent was obtained by quantification of a terminal by means of titration. A glass transition temperature was obtained according to the DSC method. A dielectric constant was calculated from an impedance value obtained with an impedance analyzer.

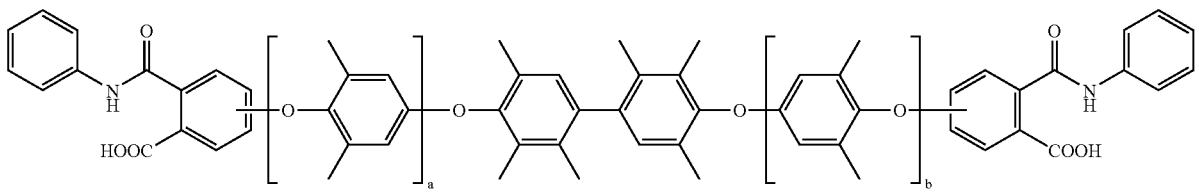

Synthesis of Acid Anhydride

A 200-ml reactor equipped with a stirrer, a thermometer and a reflux tube was charged with 30 ml of acetic acid and 0.53 g (0.0052 mol) of acetic anhydride, and the mixture was stirred under heat at 90° C. 1.00 g of the resin C was added at the time when the temperature of the reaction liquid came to 90° C., and then the resultant reaction liquid was further heated and refluxed. The heating was terminated after 10 minutes from the start of the refluxing under heat, and the reaction liquid was cooled down to room temperature. A precipitate was separated by filtration to obtain 0.20 g of an acid anhydride D having the following structure. The acid anhydride D had a number average molecular weight of 2,643 and a weight average molecular weight of 3,841. The structure was confirmed by a nuclear magnetic resonance spectrum and an infrared spectrum.

Synthesis of Bifunctional Phenylene Ether Oligomer

Synthetic Example 2

Synthetic Example 1 was repeated to obtain 2.95 kg of a resin A' represented by the formula (1). The resin A' had a number average molecular weight of 957, a weight average molecular weight of 1,539 and a hydroxyl group equivalent of 440.

Synthetic Example 3

A longitudinally long reactor having a volume of 12 liters and equipped with a stirrer, a thermometer, an air-introducing tube and baffleplates was charged with 6.64 g (29.9 mmol) of $CuBr_2$, 1.29 g (7.5 mmol) of N,N'-di-t-butyleth-

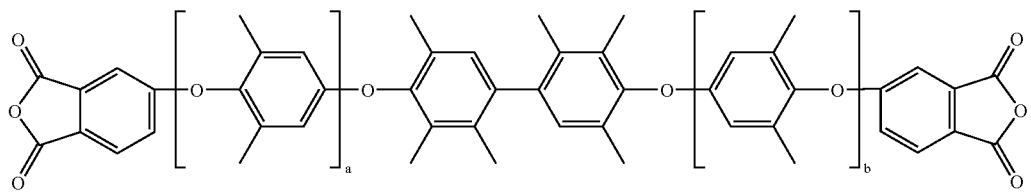

ylenediamine, 48.07 g (475.9 mmol) of n-butyldimethylamine and 2,600 g of toluene. The components were stirred at a reaction temperature of 40° C. A mixed solution (molar ratio of a bivalent phenol of the formula (2): a monovalent phenol of the formula (3)=1:10) was obtained by dissolving 129.32 g (0.48 mol) of HMBP, 584.38 g (4.79 mol) of 2,6-dimethylphenol, 0.87 g (5.1 mmol) of N,N'-di-t-butylethylenediamine and 18.69 g (185.1 mmol) of n-butyldimethylamine in 2,300 g of methanol, in advance. The mixed solution was dropwise added to the mixture in the reactor over 230 minutes while carrying out bubbling with 5.2 L/min of a mixed gas of nitrogen and air which gas had an oxygen concentration of 8%, and stirring was carried out. After the completion of the addition, 1,500 g of water in which 34.09 g (89.7 mmol) of tetrasodium ethylenediamine tetraacetate was dissolved was added to the stirred mixture to terminate the reaction. An aqueous layer and an organic layer were separated. Then, the organic layer was washed with 1.0N hydrochloric acid aqueous solution and then washed with pure water. The thus-obtained solution was concentrated by an evaporator and then dried under a reduced pressure, to obtain 702.2 g of a resin E represented by the formula (9). The resin E had a number average molecular weight of 1,490, a weight average molecular weight of 2,320 and a hydroxyl group equivalent of 750.

Synthetic Example 4

A longitudinally long reactor having a volume of 12 liters and equipped with a stirrer, a thermometer, an air-introducing tube and baffleplates was charged with 9.36 g (42.1 mmol) of $CuBr_2$, 1.81 g (10.5 mmol) of N,N'-di-t-butylethylenediamine, 67.77 g (671.0 mmol) of n-butyldimethylamine and 2,600 g of toluene. The components were stirred at a reaction temperature of 40° C. A mixed solution (molar ratio of a bivalent phenol of the formula (2): a monovalent phenol of the formula (3)=1:15) was obtained by dissolving 129.32 g (0.48 mol) of HMBP, 878.4 g (7.2 mol) of 2,6-dimethylphenol, 1.22 g (7.2 mmol) of N,N'-di-t-butylethylenediamine and 26.35 g (260.9 mmol) of n-butyldimethylamine in 2,300 g of methanol, in advance. The mixed solution was dropwise added to the mixture in the reactor over 230 minutes while carrying out bubbling with 5.2 L/min of a mixed gas of nitrogen and air which gas had an oxygen concentration of 8%, and stirring was carried out. After the completion of the addition, 1,500 g of water in which 48.06 g (126.4 mmol) of tetrasodium ethylenediamine tetraacetate was dissolved was added to the stirred mixture to terminate the reaction. An aqueous layer and an organic layer were separated. Then, the organic layer was washed with 1N hydrochloric acid aqueous solution and then washed with pure water. The thus-obtained solution was concentrated by an evaporator and then dried under a reduced pressure, to obtain 990.1 g of a resin F represented by the formula (9). The resin F had a number average molecular weight of 1,975, a weight average molecular weight of 3,514 and a hydroxyl group equivalent of 990.

Synthesis Example 5

A longitudinally long reactor having a volume of 20 liters and equipped with a stirrer, a thermometer, an air-introducing tube and baffleplates was charged with 13 g (0.12 mol) of CuCl, 707 g (5.5 mol) of di-n-butylamine and 4,000 g of methyl ethyl ketone. The components were stirred at a reaction temperature of 40° C. A solution (molar ratio of a bivalent phenol of the formula (10): a monovalent phenol of the formula (3)=1:5) was obtained by dissolving 410 g (1.6 mol) of 4,4'-methylenebis(2,6-dimethylphenol) and 977 g (8 mol) of 2,6-dimethylphenol in 8,000 g of methyl ethyl ketone, in advance. The solution was dropwise added to the mixture in the reactor over 120 minutes while carrying out bubbling with 2 L/min of air. After the completion of the addition, further, stirring was carried out for 60 minutes with continuing the bubbling with 2 L/min of air. A disodium dihydrogen ethylenediamine tetraacetate aqueous solution was added to the stirred mixture to terminate the reaction. Then, washing was carried out with 1N hydrochloric acid aqueous solution three times and then washing was carried out with ion-exchanged water. The thus-obtained solution was concentrated by an evaporator and then dried under a reduced pressure, to obtain 1,102 g of a resin G represented by the formula (9). The resin G had a number average molecular weight of 1,023, a weight average molecular weight of 1,647 and a hydroxyl group equivalent of 445.

Synthesis of Acid Anhydride

Example 2

A 200-ml reactor equipped with a stirrer, a thermometer, a dropping funnel and a reflux tube was charged with 6.31 g (0.03 mol) of trimellitic anhydride chloride and 40 g of toluene. The mixture was stirred under heat at 70° C. under nitrogen, and 8.7 g (hydroxyl group 0.019 mol) of the resin A', 0.95 g of pyridine and 80 g of toluene charged in the dropping funnel were dropwise added over 1 hour. After the completion of the dropwise addition, the mixture was further heated and refluxed for 2 hours. After the completion of the reaction, the reactor was cooled by ice bath, precipitated trimellitic anhydride chloride and pyridine hydrochloride were removed by filtration, and the filtrate was subjected to evaporation and drying under a reduced pressure, to obtain 11.6 g of an acid anhydride H represented by the formula (11). The acid anhydride H had a number average molecular weight of 1,243 and a weight average molecular weight of 2,582. The structure was confirmed by a nuclear magnetic resonance spectrum and an infrared spectrum.

Example 3

A 300-ml reactor equipped with a stirrer, a thermometer, a dropping funnel and a reflux tube was charged with 3.15 g (0.015 mol) of trimellitic anhydride chloride and 30 g of toluene. The mixture was stirred under heat at 70° C. under nitrogen, and 7.35 g (hydroxyl group 0.01 mol) of the resin E, 1.20 g of pyridine and 80 g of toluene charged in the dropping funnel were dropwise added over 1 hour. After the completion of the dropwise addition, the mixture was further heated and refluxed for 2 hours. After the completion of the reaction, the reactor was cooled by ice bath, precipitated trimellitic anhydride chloride and pyridine hydrochloride were removed by filtration, and the filtrate was subjected to evaporation and drying under a reduced pressure, to obtain 6.91 g of an acid anhydride I represented by the formula (11). The acid anhydride I had a number average molecular weight of 1,778 and a weight average molecular weight of 3,644. The structure was confirmed by a nuclear magnetic resonance spectrum and an infrared spectrum.

Example 4

A 100-ml reactor equipped with a stirrer, a thermometer, a dropping funnel and a reflux tube was charged with 0.63 g (0.003 mol) of trimellitic anhydride chloride and 5 g of toluene. The mixture was stirred under heat at 70° C. under nitrogen, and 2.05 g (hydroxyl group 0.002 mol) of the resin F, 0.25 g of pyridine and 20 g of toluene charged in the dropping funnel were dropwise added over 1 hour. After the completion of the dropwise addition, the mixture was further heated and refluxed for 2 hours. After the completion of the reaction, the reactor was cooled by ice bath, precipitated trimellitic anhydride chloride and pyridine hydrochloride were removed by filtration, and the filtrate was subjected to evaporation and drying under a reduced pressure, to obtain 2.11 g of an acid anhydride J represented by the formula (11). The acid anhydride J had a number average molecular weight of 2,243 and a weight average molecular weight of 5,487. The structure was confirmed by a nuclear magnetic resonance spectrum and an infrared spectrum.

Example 5

A 300-ml reactor equipped with a stirrer, a thermometer, a dropping funnel and a reflux tube was charged with 6.31 g (0.03 mol) of trimellitic anhydride chloride and 50 g of toluene. The mixture was stirred under heat at 70° C. under nitrogen, and 8.53 g (hydroxyl group 0.019 mol) of the resin G, 2.41 g of pyridine and 80 g of toluene charged in the dropping funnel were dropwise added over 1 hour. After the completion of the dropwise addition, the mixture was further heated and refluxed for 2 hours. After the completion of the reaction, the reactor was cooled by ice bath, precipitated trimellitic anhydride chloride and pyridine hydrochloride were removed by filtration, and the filtrate was subjected to evaporation and drying under a reduced pressure, to obtain 9.53 g of an acid anhydride K represented by the formula (11). The acid anhydride K had a number average molecular weight of 1,446 and a weight average molecular weight of 2,861. The structure was confirmed by a nuclear magnetic resonance spectrum and an infrared spectrum.

FIGS. 7 to 10 show the IR spectra of the compounds obtained in Examples 2 to 5.

FIGS. 11 to 14 show the NMR spectra of the compounds obtained in Examples 2 to 5.

Example 6

Figure 15:
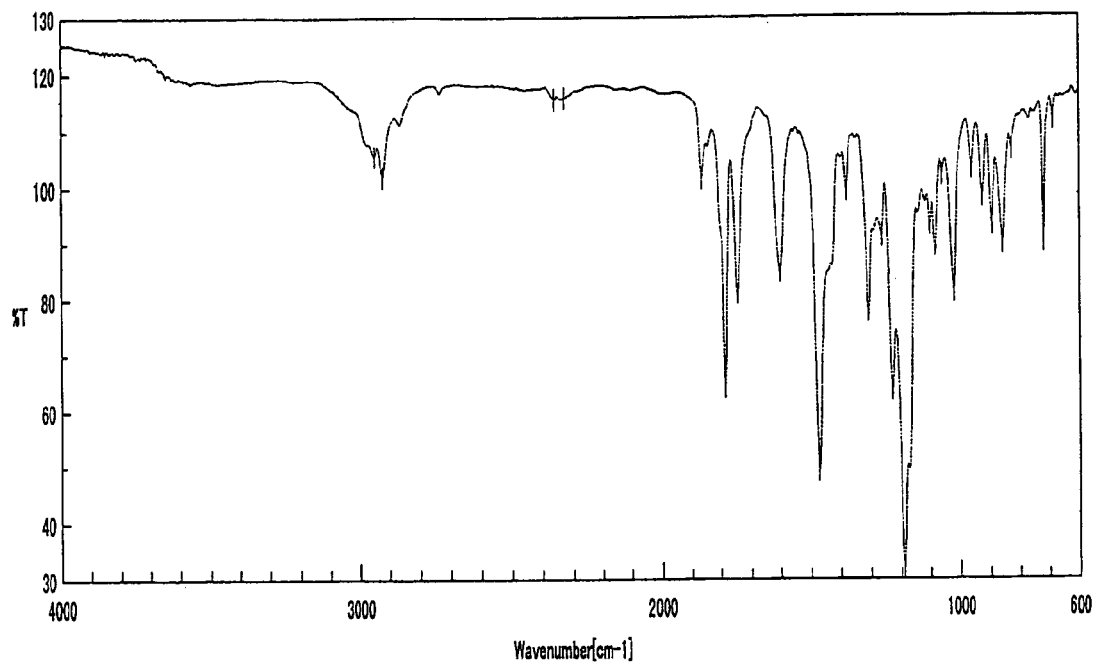
FIG. 15 shows the IR spectrum of an acid anhydride L in Example 6.
Figure 16:
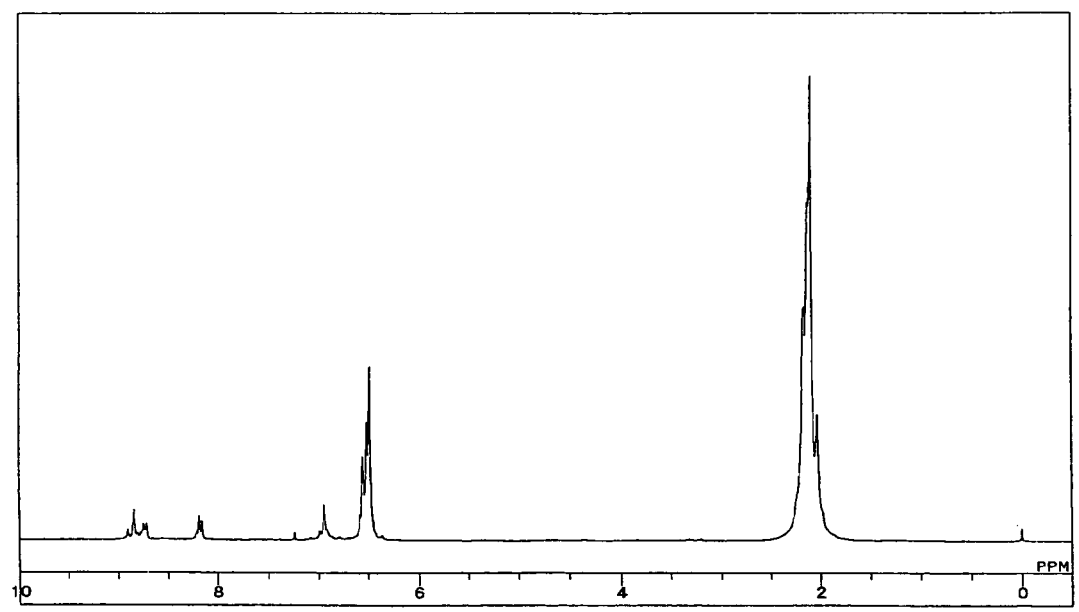
FIG. 16 shows the $^1$H-NMR spectrum of an acid anhydride L in Example 6.

A 2-liter reactor equipped with a stirrer, a thermometer, a dropping funnel, a reflux tube and a nitrogen line was charged with 63.8 g (0.30 mol) of trimellitic anhydride chloride and 442.4 g of tetrahydrofuran (THF) under nitrogen, and the mixture was cooled by ice bath. The reaction mixture was stirred under nitrogen at 5° C. or lower, and 95.0 g (hydroxyl group 0.20 mol) of the resin A', 24.6 g (0.31 mol) of pyridine and 889.4 g of THF charged in the dropping funnel were dropwise added over 150 minutes. After the completion of the dropwise addition, the reaction mixture was stirred at room temperature for 15 hours and at 40° C. for 10 hours. After the completion of the reaction, the reaction mixture was cooled by ice, precipitated trimellitic anhydride chloride and pyridine hydrochloride were removed by filtration, and the solvent was distilled off from the filtrate, to obtain 162.9 g of a solid. 651.8 g of toluene was added to the solid and the mixture was stirred for one night. Then, undissolved contents were separated by filtration, and the solvent was distilled off from the filtrate to obtain 143.0 g of a solid. 429.2 g of toluene was added to the solid to dissolve the solid, and then the resultant solution was cooled by ice. A small amount of precipitate was separated by filtration with a 0.5-µm membrane filter. Then, the solvent was distilled off from the filtrate to obtain 126.8 g of an acid anhydride L represented by the formula (11). The acid anhydride L had a number average molecular weight of 1,888 and a weight average molecular weight of 3,818. FIG. 15 shows the IR spectrum of the acid anhydride L and FIG. 16 shows the NMR spectrum of the acid anhydride L.

Synthesis of Polyimide

Example 7

The atmosphere in a 500-ml reactor equipped with a stirrer, a reflux tube, a thermometer and a nitrogen line was replaced with nitrogen. Then, the reactor was charged with 18.64 g of the acid anhydride L and 180.23 g of N-methyl-2-pyrrolidinone, and 1.72 g of tolylene diisocyanate (supplied by Nippon Polyurethane Industry Co., Ltd., Coronate T80) was dropwise added. After the completion of the dropwise addition, the mixture was stirred under heat at 115° C. under nitrogen. 6 hours later, heating was terminated and the mixture was cooled down to room temperature. The reaction mixture was dropwise added to 1 L of methanol to obtain a precipitate. Then, the precipitate was separated by filtration, and then, vacuum drying (60° C.) was carried out to obtain 17.88 g of a polyimide M. The polyimide M had a weight average molecular weight of 43,000 and a glass transition temperature of 236° C. Further, 2.68 g of the polyimide M was dissolved in 30 g of chloroform, a cast film was prepared using a 15-cm square cast board (chrome plated mirror finish board), and the cast film was measured for a dielectric constant. The dielectric constant ($\epsilon$) of the polyimide M was 2.77 (1 MHz)

Example 8

The atmosphere in a 500-ml reactor equipped with a stirrer, a reflux tube, a thermometer and a nitrogen line was replaced with nitrogen. Then, the reactor was charged with 17.96 g of the acid anhydride L, 171.23 g of N-methyl-2-pyrrolidinone, and 2.38 g of methylenediphenyl-4,4'-diisocyanate (supplied by Nippon Polyurethane Industry Co., Ltd., Millionate Mont.). The mixture was stirred under heat at 115° C. under nitrogen. 6 hours later, heating was terminated and the mixture was cooled down to room temperature. The reaction mixture was dropwise added to 1 L of methanol to obtain a precipitate. Then, the precipitate was separated by filtration and vacuum drying (60° C.) was carried out to obtain 18.22 g of a polyimide N. The polyimide N had a weight average molecular weight of 41,000 and a glass transition temperature of 231° C. Further, 2.66 g of the polyimide N was dissolved in 30 g of chloroform, a cast film was prepared using a 15-cm square cast board (chrome plated mirror finish board), and the cast film was measured for a dielectric constant. The dielectric constant ($\epsilon$) of the polyimide N was 2.75 (1 MHz).

Example 9

Figure 17:
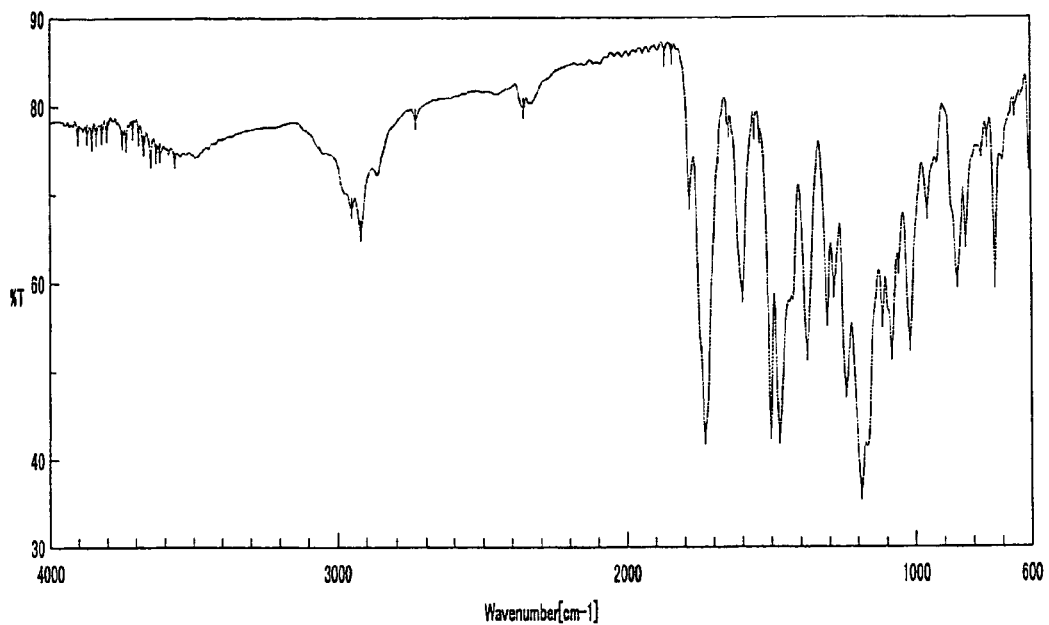
FIG. 17 shows the IR spectrum of a polyimide O in Example 9.

The atmosphere in a 300-ml reactor equipped with a stirrer, a thermometer and a nitrogen line was replaced with nitrogen. Then, the reactor was charged with 1.95 g of 4,4'-diaminodiphenyl ether and 150 ml of dimehtyl acetamide. 18.40 g of the acid anhydride L was poured to the mixture at room temperature under nitrogen. Then, the resultant mixture was heated up to 80° C. and stirred for 8 hours. The mixture was cooled down to room temperature. The reaction mixture was applied to a glass plate surface and the applied reaction mixture was dried in air at 80° C. for 20 minutes, at 150° C. for 20 minutes and at 200° C. for 20 minutes. Then, it was heat-treated at 300° C. for 1 hour under nitrogen to obtain a film of a poylimide O. The polyimide O had a weight average molecular weight of 51,000 and a glass transition temperature of 233° C. The dielectric constant ($\epsilon$) of the polyimide O was 2.79 (1 MHz). FIG. 17 shows the IR spectrum of the polyimide O.

Example 10

Figure 18:
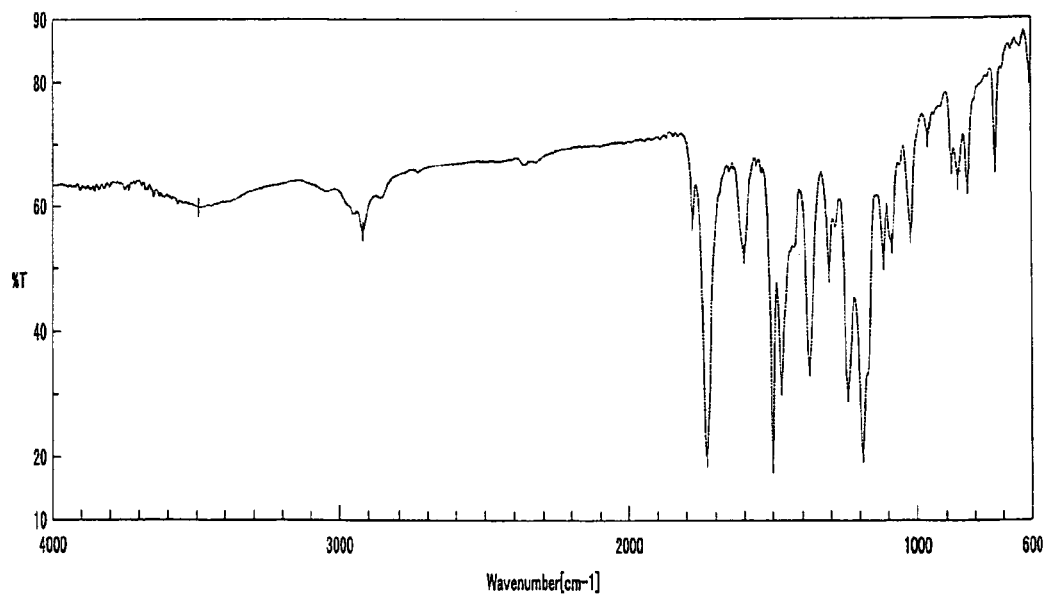
FIG. 18 shows the IR spectrum of a polyimide P in Example 10.

The atmosphere in a 300-ml reactor equipped with a stirrer, a thermometer and a nitrogen line was replaced with nitrogen. Then, the reactor was charged with 3.38 g of 4,4'-diaminodiphenyl ether and 150 ml of dimehtyl acetamide. 9.66 g of the acid anhydride L and 2.57 g of pyromellitic anhydride were poured to the mixture at room temperature under nitrogen. Then, the reaction mixture was heated up to 80° C. and stirred under heat for 9 hours, and then, the reaction mixture was cooled down to room temperature. The reaction mixture was applied to a glass plate surface and the applied reaction mixture was dried in air at 80° C. for 15 hours. Then, it was heat-treated at 300° C. for 1 hour under nitrogen to obtain a film of a poylimide P. The polyimide P had a weight average molecular weight of 46,000 and a glass transition temperature of 270° C. The dielectric constant ($\epsilon$) of the polyimide P was 2.95 (1 MHz). FIG. 18 shows the IR spectrum of the polyimide P.

Example 11

The atmosphere in a 200-ml reactor equipped with a stirrer, a thermometer and a nitrogen line was replaced with nitrogen. Then, the reactor was charged with 2.05 g of 4,4'-diaminodiphenyl ether and 40 ml of dimehtyl acetamide. 1.18 g of the acid anhydride L and 2.14 g of pyromellitic anhydride were poured to the mixture at room temperature under nitrogen. Then, the reaction mixture was stirred at room temperature for 4 hours. Then, the reaction mixture was applied to a glass plate surface and the applied reaction mixture was dried in air at 80° C. for 2 hours. Then, it was heat-treated at 300° C. for 1 hour under nitrogen to obtain a film of a poylimide Q. The polyimide Q had a weight average molecular weight of 40,000 and a glass transition temperature of 354° C. The dielectric constant ($\epsilon$) of the polyimide Q was 3.30 (1 MHz).

Example 12

The atmosphere in a 300-ml reactor equipped with a stirrer, a thermometer and a nitrogen line was replaced with nitrogen. Then, the reactor was charged with 2.02 g of p-phenylenediamine and 150 ml of dimehtyl acetamide. 10.83 g of the acid anhydride L and 2.82 g of pyromellitic anhydride were poured to the mixture at room temperature under nitrogen. Then, the reaction mixture was heated up to 80° C. and stirred under heat for 7 hours, and then, the reaction mixture was cooled down to room temperature. The reaction mixture was applied to a glass plate surface and the applied reaction mixture was dried in air at 80° C. for 17 hours. Then, it was heat-treated at 300° C. for 1 hour under nitrogen to obtain a film of a poylimide R. The polyimide R had a weight average molecular weight of 44,000 and a glass transition temperature of 262° C. The dielectric constant ($\epsilon$) of the polyimide R was 2.88 (1 MHz).

Example 13

The atmosphere in a 300-ml reactor equipped with a stirrer, a thermometer and a nitrogen line was replaced with nitrogen. Then, the reactor was charged with 2.29 g of p-phenylenediamine, 40 ml of dimehtyl acetamide, 0.10 g of triethylamine and 120 ml of γ-butyrolactone. 8.77 g of the acid anhydride L and 3.71 g of cyclohexanetetracarboxylic dianhydride were poured to the mixture at room temperature under nitrogen. Then, the reaction mixture was heated up to 180° C. and stirred under heat for 6 hours, and then, the reaction mixture was cooled down to room temperature. The reaction mixture was applied to a glass plate surface and the applied reaction mixture was dried in air at 80° C. for 15 hours. Further, it was heat-treated at 300° C. for 1 hour under nitrogen to obtain a film of a poylimide S. The polyimide S had a weight average molecular weight of 51,000 and a glass transition temperature of 266° C. The dielectric constant ($\epsilon$) of the polyimide S was 2.85 (1 MHz).

What is claimed is:
1. An acid anhydride of the formula (4),

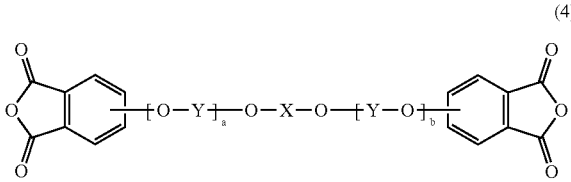

(4)

wherein anhydrides are substituted at sites 3 or sites 4,
—O—X—O— is formed of a structure defined by the formula (2),

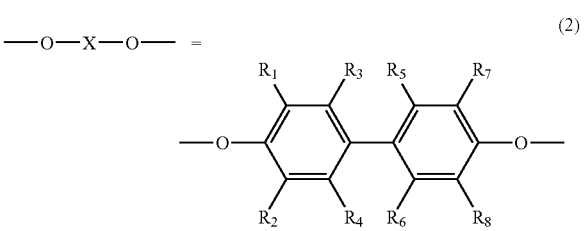

(2)

in which $R_1$, $R_2$, $R_3$, $R_7$ and $R_8$ may be the same or different and represent a halogen atom, an alkyl group having 6 or less carbon atoms or a phenyl group and $R_4$, $R_5$ and $R_6$ may be the same or different and represent a hydrogen atom, a halogen atom, an alkyl group having 6 or less carbon atoms or a phenyl group, —[Y—O]— is an arrangement of one kind of structure defined by the formula (3) or a random arrangement of at least two kinds of structures defined by the formula (3),

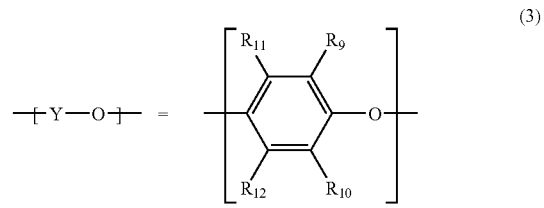

(3)

in which $R_9$ and $R_{10}$ may be the same or different and represent a halogen atom, an alkyl group having 6 or less carbon atoms or a phenyl group and $R_{11}$ and $R_{12}$ may be the same or different and represent a hydrogen atom, a halogen atom, an alkyl group having 6 or less carbon atoms or a phenyl group, and each of a and b is an integer of 0 to 30, provided that at least one of a and b is not 0, which acid anhydride is obtained from, as a raw material, a bifunctional phenylene ether oligomer having a number average molecular weight of 500 to 3,000, represented by the formula (1),

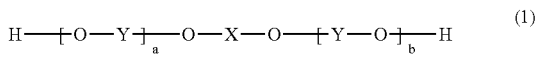 (1)

wherein —O—X—O—, —[Y—O]—, a and b are as defined in the formula [4].

2. The acid anhydride according to claim 1, wherein, in the bifunctional phenylene ether oligomer of the formula (1), —O—X—O— is represented by the formula (5) and —[Y—O]— has an arrangement structure of the formula (6) or the formula (7) or a random arrangement structure of the formula (6) and the formula (7)

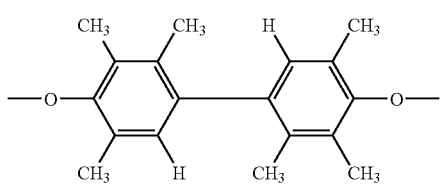 (5)

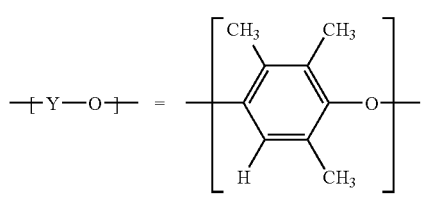 (6)

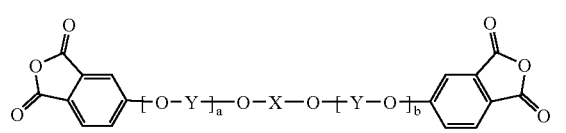 (7)

3. The acid anhydride according to claim 2, wherein —[Y—O]— has a structure represented by the formula (7).

4. The acid anhydride according to claim 3, wherein the anhydrides are substituted at sites 4

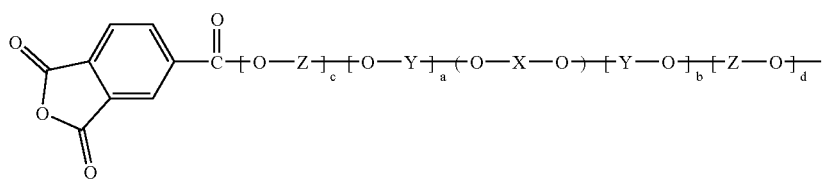 (8)

5. A polyimide obtained by reacting the acid anhydride recited in claim 1 with a diamine or a diisocyanate.

6. The polyimide according to claim 5, wherein a different bifunctional acid anhydride other than the acid anhydride recited in claim 1 is used in combination with the acid anhydride recited in claim 1.

7. The polyimide according to claim 6, wherein the different bifunctional acid anhydride is a pyromellitic anhydride derivative or a cyclohexanetetracarboxylic anhydride derivative.

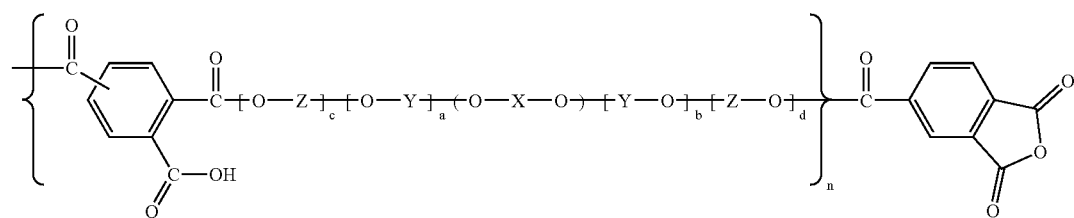 (11)

8. An acid anhydride of the formula (11),
wherein —(O—X—O)— is formed of a structure defined by the formula (2) or the formula (10),

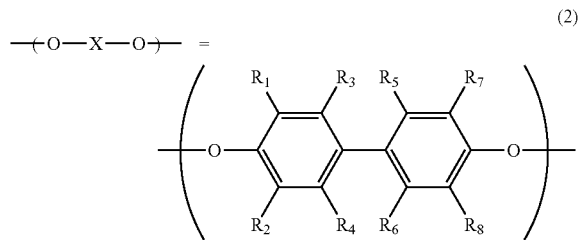
(2)

in which $R_1$, $R_2$, $R_3$, $R_7$ and $R_8$ may be the same or different and represent a halogen atom, an alkyl group having 6 or less carbon atoms or a phenyl group and $R_4$, $R_5$ and $R_6$ may be the same or different and represent a hydrogen atom, a halogen atom, an alkyl group having 6 or less carbon atoms or a phenyl group;

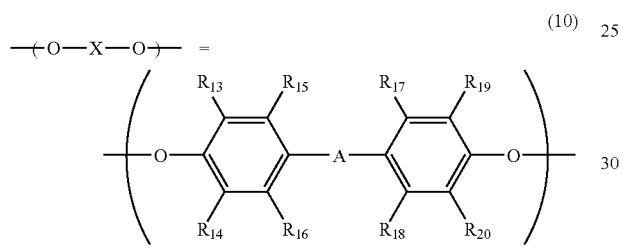
(10)

in which $R_{13}$, $R_{14}$, $R_{19}$ and $R_{20}$ may be the same or different and represent a halogen atom, an alkyl group having 6 or less carbon atoms or a phenyl group, $R_{15}$, $R_{16}$, $R_{17}$ and $R_{18}$ may be the same or different and represent a hydrogen atom, a halogen atom, an alkyl group having 6 or less carbon atoms or a phenyl group and A is a linear, branched or cyclic hydrocarbon having 20 or less carbon atoms, —(Y—O)— is an arrangement of one kind of structure defined by the formula (3) or a random arrangement of at least two kinds of structures defined by the formula (3),

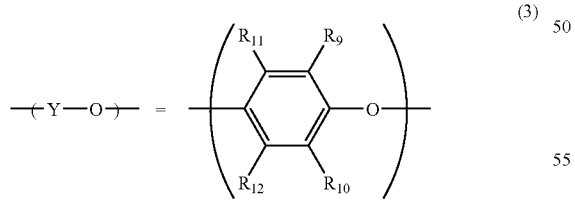
(3)

in which $R_9$ and $R_{10}$ may be the same or different and represent a halogen atom, an alkyl group having 6 or less carbon atoms or a phenyl group and $R_{11}$ and $R_{12}$ may be the same or different and represent a hydrogen atom, a halogen atom, an alkyl group having 6 or less carbon atoms or a phenyl group;

Z is an organic group having at least one carbon atom which organic group may contain an oxygen atom, a nitrogen atom, a sulfur atom or a halogen atom, each of a and b is an integer of 0 to 30, provided that at least one of a and b is not 0; and
each of c and d is 0 or 1, and
n is an integer of 0 to 10,
which acid anhydride is obtained from, as a raw material, a bifunctional phenylene ether oligomer having a number average molecular weight of 500 to 3,000, represented by the formula (9),

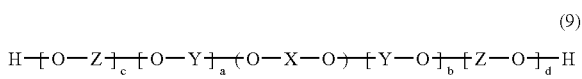
(9)

wherein —(O—X—O)—, —(Y—O)—, Z, a, b, c and d are as defined in the formula (11).

9. The acid anhydride according to claim 8,
wherein, in the bifunctional phenylene ether oligomer represented by the formula (9), —(O—X—O)— is represented by the formula (5) or the formula (12) and —(Y—O)— has an arrangement structure of the formula (6) or the formula (7) or a random arrangement structure of the formula (6) and the formula (7),

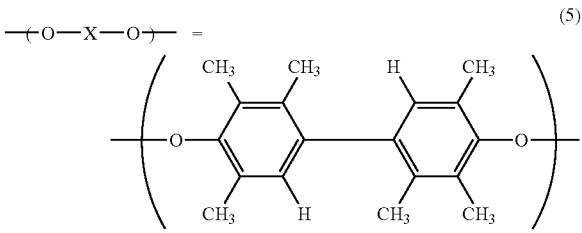
(5)

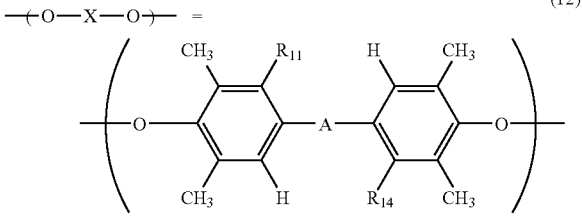
(12)

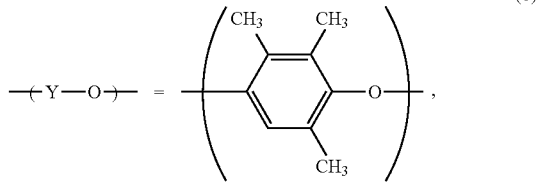
(6)

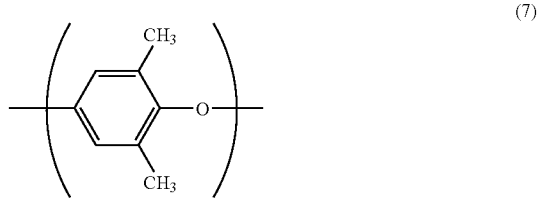
(7)

wherein $R_{11}$ and $R_{14}$ represent a hydrogen atom or a methyl group and A is a linear, branched or cyclic hydrocarbon having 20 or less carbon atoms.

10. The acid anhydride according to claim 8,
wherein —(Y—O)— has a structure represented by the formula (7).

11. A polyimide obtained by reacting the acid anhydride recited in claim 8 with a diamine or a diisocyanate.

12. The polyimide according to claim 11, wherein a different bifunctional acid anhydride other than the acid anhydride recited in claim 8 is used in combination with the acid anhydride recited in claim 8.

13. The polyimide according to claim 12, wherein the different bifunctional acid anhydride is a pyromellitic anhydride derivative or a cyclohexanetetracarboxylic anhydride derivative.

* * * * *